US011065220B2

(12) United States Patent
Hale et al.

(10) Patent No.: US 11,065,220 B2
(45) Date of Patent: Jul. 20, 2021

(54) ANTI-PATHOGENIC THERAPEUTIC COMPOSITIONS

(71) Applicant: Wintermute Biomedical, Inc., Corvallis, MT (US)

(72) Inventors: Weston J. Hale, Missoula, MT (US); Thomas F. Rau, Heidelberg Heights (AU)

(73) Assignee: Wintermute Biomedical, Inc., Corvallis, MT (US)

( * ) Notice: Subject to any disclaimer, the term of this patent is extended or adjusted under 35 U.S.C. 154(b) by 0 days.

(21) Appl. No.: 16/485,735

(22) PCT Filed: Feb. 13, 2018

(86) PCT No.: PCT/US2018/018077
§ 371 (c)(1),
(2) Date: Aug. 13, 2019

(87) PCT Pub. No.: WO2018/148763
PCT Pub. Date: Aug. 16, 2018

(65) Prior Publication Data
US 2020/0046666 A1    Feb. 13, 2020

Related U.S. Application Data

(60) Provisional application No. 62/458,140, filed on Feb. 13, 2017.

(51) Int. Cl.
*A61K 31/198* (2006.01)
*A61P 31/04* (2006.01)
*A61K 9/00* (2006.01)
*A61K 31/192* (2006.01)
*A61K 31/201* (2006.01)
*A61K 47/10* (2017.01)

(52) U.S. Cl.
CPC .......... *A61K 31/198* (2013.01); *A61K 9/0014* (2013.01); *A61K 31/192* (2013.01); *A61K 31/201* (2013.01); *A61K 47/10* (2013.01); *A61P 31/04* (2018.01)

(58) Field of Classification Search
CPC ............................ A61K 31/198; A61P 31/04
USPC ........................................................ 514/560
See application file for complete search history.

(56) References Cited

U.S. PATENT DOCUMENTS

| 4,150,052 | A  |   | 4/1979  | Watson et al. |
|-----------|----|---|---------|---------------|
| 5,260,066 | A  |   | 11/1993 | Wood et al.   |
| 5,766,614 | A  |   | 6/1998  | Yong          |
| 6,015,798 | A  |   | 1/2000  | Ogilvie et al.|
| 6,841,174 | B2 |   | 1/2005  | Shalaby et al.|
| 7,288,265 | B1 |   | 10/2007 | Rolf          |
| 10,195,242| B2 | * | 2/2019  | Hale ............ A61P 31/04 |
| 2006/0159746 | A1 | | 7/2006 | Troup et al. |

| 2007/0258913 | A1 | 11/2007 | Rossel |
| 2008/0026974 | A1 | 1/2008 | Barnhart et al. |
| 2009/0068128 | A1 | 3/2009 | Waddington |
| 2010/0111879 | A1 | 5/2010 | Tamarkin et al. |
| 2011/0034557 | A1 | 2/2011 | Jarrell et al. |
| 2012/0328544 | A1 | 12/2012 | Stockel et al. |
| 2016/0066578 | A1 | 3/2016 | Ala'Aldeen et al. |

FOREIGN PATENT DOCUMENTS

| CN | 1969984 A | 5/2007 | |
| CN | 101991726 A | 3/2011 | |
| CN | 102178842 A | 9/2011 | |
| EP | 1842437 A1 * | 10/2007 | ........... A61K 31/198 |
| EP | 1595936 B1 | 10/2011 | |
| GB | 2051574 A | 1/1981 | |
| JP | 11-269034 A | 10/1999 | |
| JP | 2000281528 A | 10/2000 | |
| JP | 2002114670 A | 4/2002 | |
| WO | WO2004/026840 A1 | 4/2004 | |
| WO | WO2005/049553 A1 | 6/2005 | |
| WO | WO2005/123101 A1 | 12/2005 | |
| WO | WO2006/046025 A1 | 5/2006 | |
| WO | WO2008/111532 A1 | 9/2008 | |
| WO | WO2012/090205 A2 | 7/2012 | |
| WO | WO2018/148763 A1 | 8/2018 | |
| WO | WO2020/072479 A1 | 4/2020 | |

OTHER PUBLICATIONS

Angele et al.; L-arginine: a unique amino acid for improving depressed wound immune function following hemorrhage; European Surgical Research; 34(1-2); pp. 53-60; Jan.-Apr. 2002.

Atilano et al.; Wall teichoic acids of *Staphylococcus aureus* limit recognition by the *Drosophila peptidoglycan* recognition protein-SA to promote pathogenicity; Plos Pathogens; 7(12); ; 13 pages; e1002421; Dec. 1, 2011.

Bourne et al.;Effect of Undecylenic Acid as a Topical Microbicide Against Genital Herpes Infection in Mince and Guinea Pigs; Antiviral Research; 40(3); pp. 139-144; Jan. 1, 1999.

Brown et al.; Methicillin resistance in *Staphylococcus aureus* requires glycosylated wall teichoic acids; Proceedings of the National Academy of Sciences; 109(46); pp. 18909-18914; (Author Manuscript); Nov. 13, 2012.

Brown et al.; *Staphylococcus aureus* and Bacillus subtilis W23 make polyribitol wall teichoic acids using different enzymatic pathways; Chemistry and Bilogy; 17(10); pp. 1101-1110; Oct. 29, 2010.

(Continued)

*Primary Examiner* — Kevin E Weddington
(74) *Attorney, Agent, or Firm* — Shay Glenn LLP

(57) ABSTRACT

Therapeutic compounds useful for the treatment of pathogens including bacteria (gram positive and gram negative, mycobacteria), some fungi and viruses. The compounds described herein may include a mixture of therapeutically-effective amounts of a polar amino acid, a Cl 1 fatty acid, and an anthraquinone. The invention further provides for the administration of the therapeutic compounds to a patient (e.g., a human) suffering from an infection.

17 Claims, 13 Drawing Sheets

(56) References Cited

OTHER PUBLICATIONS

Chung et al.; Rhein affects arylamine N-acetyltransferase activity in Helicobacter pylori from peptic ulcer patients; Journal of Applied Toxicology; 18(2); pp. 117-123; Mar. 1, 1998.

Ding et al.;Screening for Novel Quorum-Sensing Inhibitors to Interfere with the Formation of Pseudomonas aeruginosa Biofilm; Journal of Medical Microbiology; 60(12); pp. 1827-1834; Dec. 1, 2011.

Diep et al.; Complete genome sequence of USA300, an epidemic clone of community-acquired meticillin-resistant *Staphylococcus aureus*; The Lancet; 367(9512); pp. 731-739; Mar. 4, 2006.

Diep et al.; The arginine catabolic mobile element and staphylococcal chromosomal cassette mec linkage: convergence of virulence and resistance in the USA300 clone of methicillin-resistant *Staphylococcus aureus*; The Journal of Infectious Diseases; 197(11); pp. 1523-1530; Jun. 1, 2008.

drugs.com; Rhubarb; 8 pages; retrieved from the internet (https://www.drugs.com/npp/rhubarb.html) on May 8, 2018.

Garcia-Sosa et al.; Chrysophanol, an antimicrobial anthraquinone from the root extract of colubrina greggii; Journal of the Mexican Chemical Society; 50(2); pp. 76-78; Jun. 2006.

Green et al.; Nitric oxide: cytokine-regulation of nitric oxide in host resistance to intracellular pathogens; Immunology Letter; 43(1-2); pp. 87-94; Dec. 1, 1994.

Handa et al.; (Ed); Extraction technologies for medicinal and aromatic plants; United Nations Industrial Development Organization and the International Centre for Science and High Technology, Trieste; 266 pages; (year of pub. sufficiently earlier than effective US filed and any foreign priority date); 2008.

Helms et al.; Natural Treatment of Chronic Rhinosinusitis; Alternative Medicine Reviews; 11(3); pp. 196-207; Sep. 1, 2006.

Lai et al.; Rhein induced apoptosis through the endoplasmic reticulum stress, caspase- and mitochondria-dependent pathways in SCC-4 human tongue squamous cancer cells; In Vivo; 23(2); pp. 309-316; Mar. 1, 2009.

Lee et al.; Synergistic effect of emodin in combination with ampicillin or oxacillin against methicillin-resistant *Staphylococcus aureus*; Pharmaceutical Bilogy; 48(11); pp. 1285-1290; Nov. 1, 2010.

Li et al.; Potent In Vitro Antifungal Activities of Naturally-Occurring Acetylenic Acids; Antimicrobial Agents and Chemotherapy; 52(7); pp. 2442-2448; Jul. 1, 2008.

MacMicking et al.; Identification of nitric oxide synthase as a protective locus against tuberculosis; Proceedings of the National Academy of Sciences; 94(10); pp. 5243-5248; May 13, 1997.

MacMicking et al.; Nitric oxide and macrophage function; Annual Review of Immunology; 15(1); pp. 323-350; Apr. 15, 1997.

McLain et al.; Undecylenic Acid Inhibits Morphogenesis of Candida albicans; Antimicrobial Agents and Chemotherapy; 44(10); pp. 2873-2875; Oct. 1, 2000.

Mohamed et al.; Antibacterial activity of novel cationic peptides against clinical isolates of multi-drug resistant *Staphylococcus pseudintermedius* from infected dogs; PloS one; 9(12); 20 pages; DOI:10.1371/journal.pone.0116259; Dec. 31, 2014.

Monograph; Undecylenic Acid; , Alternative Medicine Review; 7(1); pp. 68-70; Feb. 2002.

Morris; Enzymes of arginine metabolism; The Journal of Nutritiion; 134 (10); pp. 2743S-2747S; Oct. 1, 2004.

Nakaki et al.; L-arginine-induced hypotension; The Lancet; 336(8716); pp. 696; Sep. 15, 1990.

Nelson; Undecylenic acid in the treatment of psoriasis and neurodermatitis; California Medicine; 74(1); pp. 17; Jan. 1951.

Rattner et al.; Treatment of psoriasis with undecylenic acid by mouth; Journal of the American Medical Association; 146(12); pp. 1113-1115; Jul. 21, 1951.

Seguin et al.; Induction of nitric oxide synthase protects against malaria in mice exposed to irradiated Plasmodium berghei infected mosquitoes: involvement of interferon gamma and CD8+ T cells; Journal of Experimental Medicine; 180(1); pp. 353-358; Jul. 1, 1994.

Shafran et al.; Topical undecylenic acid for herpes simplex labialis: a multicenter, placebo-controlled trial; Journal of Infectious Diseases; 176(1); pp. 78-83; Jul. 1, 1997.

Testa et al.; Hydrolysis in drug and prodrug metabolism: Chemistry, Biochemistry, and Enzymology; Wiley-VCH, Zurich, Switzerland, 2003; 11 pages; retrieved from the interent (http://sutlib2.sut.ac.th/sut_contents/H89132.pdf); on May 8, 2018.

Thurlow et al.; Functional Modularity of the Arginine Catabolic Mobil Element Contributes to the Success of USA300 Methicillin-Resistant *Staphylococcus aureus*; Cell Host and Microbe; 13(1); pp. 100-107; (Author Manuscript); Jan. 16, 2013.

Wrong; Undecylenic acid administered orally in the treatment of psoriasis; Can. Med. Assoc. J..; 63(6); pp. 543-545; Dec. 1950.

Wu et al.; Antimicrobial properties and toxicity of anthraquinones by microcalorimetric bioassay; Chinese Journal of Chemistry; 24(1); pp. 45-50; Jan. 1, 2006.

Yu et al.; Global transcriptional response of *Staphylococcus aureus* to rhein, a natural plant product; Journal of Biotechnology; 135(3); pp. 304-308; Jun. 30, 2008.

Rau et al.; U.S. Appl. No. 16/836,881 entitled "Therapeutic compositions of undecylenic acid and arginine," filed Mar. 31, 2020.

Rau et al.; U.S. Appl. No. 16/836,893 entiteld "Therapeutic compositions of decylenic acid and arginine," filed Apr. 1, 2020.

Hatano et al.; Phenolic Constituents of Cassia Seeds and Antibacterial Effect of Some Naphthalenes and Antraquipones on Methicillin-Resistant *Staphylococcus aureus*: Chemical and Pharmaceutican Bulletin; Pharmaceutical Society of Japan; 47(8): pp. 1121-1127; Jan. 1, 1999.

Kosikowska et al.; Antimicrobiai Activity and Total Content of Polvohenols or *Rheum* L. species Growing in Poland; Central European Journal of Biology; 5(6); pp. 814-820; Dec. 1, 2010.

* cited by examiner

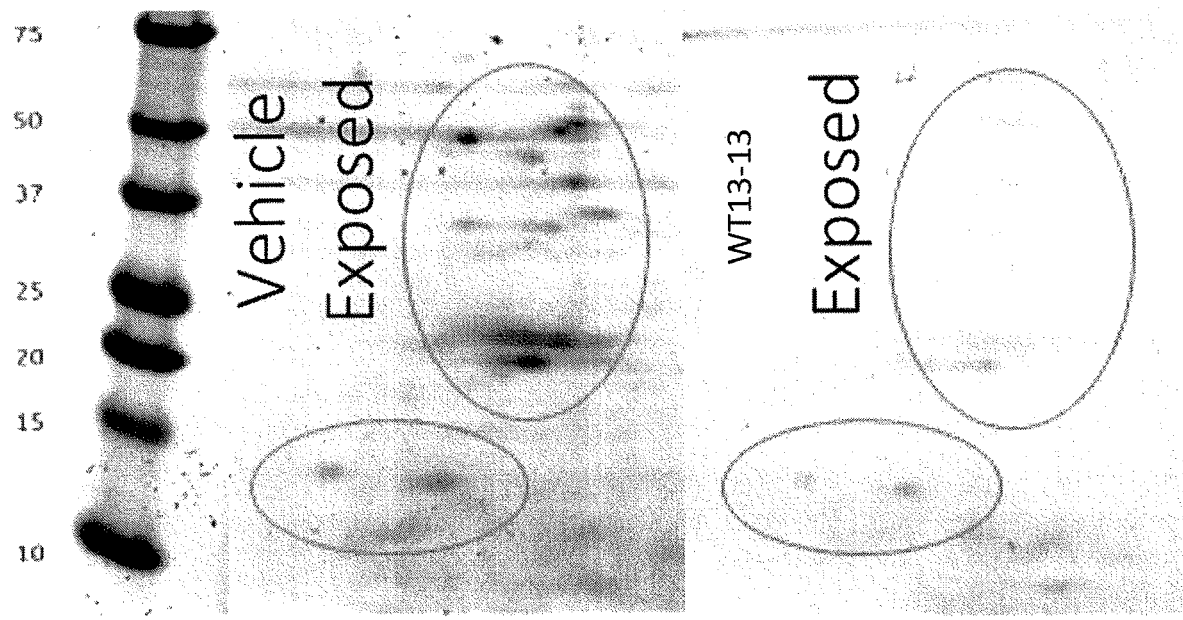
FIG. 13  FIG. 14
FIG. 15A
FIG. 15B

ANTI-PATHOGENIC THERAPEUTIC COMPOSITIONS

CROSS REFERENCE TO RELATED APPLICATIONS

This patent application claims priority to U.S. Provisional Patent Application No. 62/458,140, filed on Feb. 13, 2017, and titled "ANTIBACTERIAL COMPOUNDS." This application is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Pathogens, such as bacteria, viruses, or other microorganisms that can cause disease, are increasingly difficult to treat, particularly with the increasing advent of antibiotic resistant forms of pathogens. The United States Center for Disease Control (CDC) publishes a list of pathogenic threats, many of which include drug-resistant microorganisms and microorganisms for which no effective drug therapy exists. For example, bacterial infections of the skin and underlying tissue present a significant clinical treatment issue. These types of infections commonly involve gram-positive bacteria that colonize on the skin and underlying tissue and symptoms can range from mild discomfort to death. Bacteria cause a number of skin conditions such as impetigo, cellulitis, boils, and acne. Deep tissue infections of surgical wounds or traumatic wounds can invade the blood stream leading to septicemia and death.

Currently, many skin infections that are caused by gram-positive bacteria are aggressively treated with antibiotics. However, as strains of pathogenic bacteria develop antibiotic resistance mechanisms, it becomes crucial to develop novel therapies that inhibit bacterial growth without using traditional antibiotics. In recent years, the issue of bacterial antibiotic resistance has become much more recognized with the development of so-called 'superbugs' such as methicillin-resistant *Staphylococcus aureus* (MRSA) and vancomycin-resistant *enterococcus* (VRE). These bacteria are common skin pathogens that have developed significant antibiotic resistance. With the continued use of antibiotics in both humans and animals bred for consumption, many common strains of skin bacteria are developing widespread antibiotic resistance leading to a serious health care issues. Common bacteria that are implicated in skin infections are Methicillin resistant *Staphylococcus aureus*, *S. pyogenes* and *S. pneumoniae*, *E. faecalis* and *S. agalactiae*. As these bacteria colonize the skin they break down the epidermis, induce an inflammatory response, and if untreated, invade into deeper tissue causing cellulitis. In extreme cases the bacteria invade the circulatory system causing sepsis and possible death.

It has become evident to the medical community that novel treatments must be developed to address this issue. However, many pharmaceutical companies have not aggressively pursued the development of new, antimicrobial treatments for skin and wound infections.

Described herein are compounds and methods of using them to treat a number of pathogens, including both gram negative and gram positive bacteria, fungi and viruses.

SUMMARY OF THE DISCLOSURE

The present invention relates to anti-pathogenic (e.g., antibacterial and/or antiviral and/or antifungal and/or antimicrobial) compounds and methods of using them. The compounds and methods of making and using them described herein are based, in part, on the discovery of mixtures of one or more polar (hydrophilic) amino acids, one or more anthraquinones and one or more 11 carbon (C11) fatty acids to form a mixture of specific ranges of ratios or percentages of the mixture, which exhibits surprising anti-pathogenic therapeutic properties. Surprisingly, outside of these defined ranges the anti-pathogenic activity is significantly lost, particularly with respect to certain categories of pathogens, including in particular the gram negative bacteria (e.g., gram negative rod, or GNR, bacteria). As will be described in greater detail herein, the anti-pathogenic compounds described herein (which may also be referred to herein as anti-pathogenic agents) are effective against a broad variety of pathogens including in particular the gram negative and gram positive bacteria, fungi and viruses. These anti-pathogenic compounds may be used to treat or prevent infections, including bacterial infections, in, e.g., a human or non-human patient. These anti-pathogenic compounds may be used to kill, stop or slow the progression of a pathogenic infection (or to kill and/or slow or stop the growth of a pathogen in or on a body or material, such as a surface). For example, described herein are bacteriostatic compositions that include a mixture of polar amino acids, C11 fatty acids, and anthraquinones, each class of components within a defined percentage of the mixture; additional materials (excipient, diluent, or carrier) may be combined with the mixture to form the anti-pathogenic compound. In some variations, the amino acid includes L-arginine, the C11 fatty acid includes undecylenic acid, and the anthraquinone includes cassic acid (rhein).

As will be described in detail herein, an anti-pathogenic therapeutic composition may typically include a mixture of L-Arginine, undecylenic acid and cassic acid, wherein the percentage of cassic acid in the mixture is greater than 0.03% w/w of the mixture. For example, an anti-pathogenic (e.g., bactericidal) composition that is effective against gram negative (and effective against both gram positive and gram negative bacteria) may contain a polar amino acid, a C11 fatty acid, and an anthraquinone. The polar amino acid may be L-arginine, the C11 fatty acid may be undecylenic acid, and the anthraquinone may be cassic acid (e.g., rhein). The percentage of anthraquinone in the mixture may generally be between about 0.03% and about 2.3% w/w of the mixture (e.g., between about 0.1% and about 1% w/w of the mixture, e.g., about 0.4% w/w of the mixture). The concentration of the anthraquinone may be, e.g., greater than 0.1 mg/ml (e.g., greater than about 0.3 mg/ml, greater than about 0.5 mg/ml, greater than about 0.7 mg/ml, greater than about 0.8 mg/ml, greater than about 0.9 mg/ml, greater than about 1 mg/ml, etc.). The percentage of polar amino acid may be between 47% and 73% w/w of the mixture (e.g., about 62% w/w of the mixture). The percentage of C11 fatty acid in the mixture may be between about 26% and about 53% w/w of the mixture (e.g., about 37.6% w/w of the mixture). Any of these mixtures may be combined with an excipient, diluent, or carrier.

Any of the anti-pathogenic compositions described herein may be used to treat a patient, e.g., a human or non-human patient, suffering from or at risk of developing a bacterial infection by administering a therapeutically effective amount of one or more of the anti-pathogenic compositions described herein including one or more polar amino acids, one or more C11 fatty acids, and one or more anthraquinones. For example, described herein are methods of treating a patient, e.g., a human or non-human patient, suffering from or at risk of developing a bacterial infection by administering a therapeutically effective amount of a composition that contains one or more polar amino acids, one or more C11 fatty acids, and one or more anthraquinones, in which the total percentage of the one or more anthraquinone in the mixture is greater than 0.03% w/w of the mixture.

Any of the anti-pathogenic compositions described herein may be part of a kit that includes one or more of the anti-pathogenic compositions along with instructions for administration to a patient.

The one or more polar amino acids may include, e.g., one or more of: arginine, asparagine, asparatate, glutamate, glutamine, histidine, serine, threonine and lysine. C11 fatty acids may be saturated or unsaturated. For example, a saturated C11 fatty acid can be, e.g., undecylenic acid (e.g., undecanoic acid). An anthraquinone can be cassic acid (e.g., rhein), emodin, chrysophanol, physcion, dantron, cascarin, catenarin, and/or diacerein.

Any of these compositions may include a cooling or heating additive, such as menthol. The compositions may contain a pharmaceutically acceptable excipient, diluent, or carrier in addition to the mixture. The amount of excipient, diluent, or carrier does not change the relative ratios (percentages) of the polar amino acids, C11 fatty acids and anthraquinones in the mixture.

For example, an anti-pathogenic therapeutic composition effective against gram negative (e.g., gram negative and also gram positive) bacteria may include: mixture of L-Arginine, undecylenic acid and cassic acid, wherein the percentage of cassic acid in the mixture is greater than 0.03% w/w of the mixture. For example, an anti-pathogenic therapeutic composition effective against gram negative bacteria may include a mixture of L-Arginine, undecylenic acid and cassic acid, wherein the percentage of cassic acid in the mixture is between 0.03% and 2.3% w/w of the mixture, the percentage of L-Arginine is between 47% and 73% w/w of the mixture, and the percentage of undecylenic acid in the mixture is between 26% and 53% w/w of the mixture, further wherein the mixture is combined with an excipient, diluent, or carrier. An anti-pathogenic therapeutic composition effective against gram negative bacteria may include a mixture of L-Arginine, undecylenic acid and cassic acid, wherein the percentage of cassic acid in the mixture is between 0.1% and 1.0% w/w of the mixture, the percentage of L-Arginine is between 47% and 73% w/w of the mixture, and the percentage of undecylenic acid in the mixture is between 26% and 53% w/w of the mixture, further wherein the mixture is combined with an excipient, diluent, or carrier and the concentration of cassic acid in the composition is 0.1 mg/ml or greater.

The percentage of cassic acid in the mixture may be between about 0.03% and about 2.3% w/w of the mixture. For example, the percentage of cassic acid in the mixture may be between about 0.1% and about 1.0% w/w of the mixture (e.g., about 0.4% w/w of the mixture).

The percentage of L-Arginine in the mixture may be between about 47% and about 73% w/w of the mixture (e.g., about 62% w/w of the mixture).

The percentage of undecylenic acid in the mixture may be between about 26% and about 53% w/w of the mixture (e.g., about 37.6% w/w of the mixture).

As mentioned, any of these anti-pathogenic therapeutic compositions may include, combined with the mixture, an excipient, diluent, or carrier. The excipient, diluent, or carrier may comprise cetyl alcohol and water. The excipient, diluent, or carrier may be configured for topical application. For example, the excipient, diluent, or carrier may comprise an emulsifying agent. In general, an excipient, diluent or carrier (including water) is an inactive substance that serves as the vehicle or medium for a drug or other active substance. Excipients may include bulking agents, fillers or the like. The excipient may aid in the handling of the mixture of active substances by facilitating powder flowability or non-stick properties, aiding in vitro stability (e.g., prevention of denaturation or aggregation over the expected shelf life), enhancing solubility, improving absorption and/or uptake, providing better aesthetic and/or cosmetic features, altering physical properties etc.

Examples of excipients may include: antiadherents (e.g., magnesium stearate, etc.); binders (e.g., saccharides and their derivatives: disaccharides, sucrose, lactose; polysaccharides and their derivatives: starches, cellulose or modified cellulose such as microcrystalline cellulose and cellulose derivatives including cellulose ethers such as hydroxypropyl cellulose; sugar alcohols such as xylitol, sorbitol or mannitol; protein: gelatin; synthetic polymers: polyvinylpyrrolidone or PVP, polyethylene glycol or PEG, polyvinylpyrrolidone, starch, sucrose and polyethylene glycol, methyl cellulose); coatings (e.g., cellulose ether hydroxypropyl methylcellulose, synthetic polymers, shellac, corn protein zein or other polysaccharides, gelatin); enterics (fatty acids, waxes, shellac, plastics, and plant fibers); colors (titanium oxide, azo dyes, etc.); disintegrants (e.g., cross-linked polymers: crosslinked polyvinylpyrrolidone such as crospovidone, crosslinked sodium carboxymethyl cellulose or croscarmellose sodium, glycolate, etc.); flavors (fruit extract, etc.); glidants (e.g., fumed silica, talc, and magnesium carbonate, etc.); lubricants (e.g., talc or silica, and fats, e.g. vegetable stearin, magnesium stearate or stearic acid, etc.; preservatives (e.g., antioxidants like vitamin A, vitamin E, vitamin C, retinyl palmitate, and selenium; cysteine, methionine; citric acid, sodium citrate; parabens: methyl paraben and propyl paraben); sorbents; sweeteners (e.g., sugar); vehicles (petrolatum, dimethyl sulfoxide, mineral oil, etc.); emollient/stiffening agents (Carnauba wax, Cetyl alcohol, Cetyl ester wax, Emulsifying wax, Hydrous lanolin, Lanolin, Lanolin alcohols, Microcrystalline wax, Paraffin, Petrolatum, Polyethylene glycol, Stearic acid, Stearyl alcohol, White wax, Yellow wax, etc.); emulsifier/emulsifying agent/solubilizing agent (Polysorbate 20, Polysorbate 80, Polysorbate 60, Poloxamer, Emulsifying wax, Sorbitan monostearate, Sorbitan monooleate, Sodium lauryl sulfate, Propylene glycol monostearate, Diethylene glycol monoethyl ether, Docusate sodium, etc.); humectant (e.g., Glycerin, Propylene glycol, Polyethylene glycol, Sorbitol solution, 1,2,6 Hexanetriol, etc.); thickening/gelling agent (Carbomer, Methyl cellulose, Sodium carboxyl methyl cellulose, Carrageenan, Colloidal silicon dioxide, Guar gum, Hydroxypropyl cellulose, Hydroxypropyl methyl cellulose, Gelatin, Polyethylene oxide, Alginic acid, Sodium alginate, Fumed silica, etc.); preservative (Benzoic acid, Propyl paraben, Methyl paraben, Imidurea, Sorbic acid, Potassium sorbate, Benzalkonium chloride, Phenyl mercuric acetate, Chlorobutanol, Phenoxyethanol, etc.); permeation enhancer (Propylene glycol, Ethanol, Isopropyl Alcohol, Oleic acid, Polyethylene glycol, etc.); chelating agent (Ethylene diamine tetraacetate, etc.); acidifying/alkalizing/buffering agent (Citric acid, Phosphoric acid, Sodium hydroxide, Monobasic sodium Phosphate, Trolamine, etc.); vehicle/solvent (Purified water, Hexylene glycol, Propylene glycol, Oleyl alcohol, Propylene carbonate, Mineral oil, etc.). These examples may be redundant, and different excipients may be used for different reasons, and may have dual or multiple functionalities.

In general, the concentration of cassic acid in the composition may be greater than a minimum concentration, e.g., of about 0.1 mg/ml (e.g., about 0.2 mg/ml, about 0.3 mg/ml, about 0.4 mg/ml, about 0.5 mg/ml, about 0.6 mg/ml, about 0.7 mg/ml, about 0.8 mg/ml, about 0.9 mg/ml, about 1 mg/ml, etc.). In general, antiviral specific compositions may have a much lower minimum concentration of anthraquinone (including cassic acid). For example, an antiviral therapeutic composition may include greater than about 0.0001 mg/ml, greater than 0.0005 mg/ml, greater than about 0.001 mg/ml, greater than about 0.005 mg/ml, greater than about 0.01 mg/ml, greater than about 0.05 mg/ml, etc.).

The composition may be configured as a liquid or emulsion in a form suitable for topical administration to a human, including a spray, lotion, cream, ointment, tincture, etc.

Also described herein are methods of treating a patient to destroy a pathogen using an anti-pathogenic agent effective against gram negative and gram positive bacteria, viruses and fungi. For example, the method may include: administering to said patient, a therapeutically effective amount of the anti-pathogenic agent, the anti-pathogenic agent comprising a mixture of L-Arginine, undecylenic acid and cassic acid, wherein the percentage of cassic acid in the mixture is greater than 0.03% w/w of the mixture. A method of treating a patient to destroy a pathogen using an anti-pathogenic agent effective against gram negative and gram positive bacteria, virus or fungi may include: administering to said patient, a therapeutically effective amount of the anti-pathogenic agent, the anti-pathogenic agent comprising a mixture of L-Arginine, undecylenic acid and cassic acid, wherein the percentage of cassic acid in the mixture is between 0.03% and 2.3% w/w of the mixture, the percentage of L-Arginine is between 47% and 73% w/w of the mixture, and the percentage of undecylenic acid in the mixture is between 26% and 53% w/w of the mixture, further wherein the mixture is combined with an excipient, diluent, or carrier.

Administering may comprise applying the anti-pathogen agent to the patient's skin, to the patient's wound, etc. For example, administering may comprise spraying the anti-pathogen agent on the patient. Alternatively or additionally, administering may comprise applying the anti-pathogenic agent systemically to the patient. The compositions described herein may also be used as a coating (e.g., to a medical device, implant, etc.).

The pathogen may be one or more of: a gram negative bacteria, a gram positive bacteria, a fungus, a Mycobacteria, a *pneumoniae* bacteria, an *E. coli* bacteria, and/or a virus.

The percentage of cassic acid in the mixture may be between about 0.03% and about 2.3% w/w of the mixture (e.g., between about 0.1% and about 1.0% w/w of the mixture, about 0.4% w/w of the mixture, etc.). The percentage of L-Arginine in the mixture may be between about 47% and about 73% w/w of the mixture (e.g., about 62% w/w of the mixture). The percentage of undecylenic acid in the mixture may be between about 26% and about 53% w/w of the mixture (e.g., about 37.6% w/w of the mixture).

The anti-pathogenic agent may further comprise an excipient, diluent, or carrier, such as cetyl alcohol and water.

The excipient, diluent, or carrier may be configured for topical application. The excipient, diluent, or carrier may comprise an emulsifying agent. The anti-pathogenic agent may be configured as a liquid or emulsion in a form suitable for topical administration to a human. The anti-pathogenic agent may further comprise a cooling or heating additive. The concentration of cassic acid in the anti-pathogenic agent may be greater than 0.1 mg/ml.

For example, a method of treating a patient to destroy a pathogen using an anti-pathogenic agent effective against gram negative bacteria may include: administering to said patient, a therapeutically effective amount of the anti-pathogenic agent, the anti-pathogenic agent comprising a mixture of L-Arginine, undecylenic acid and cassic acid, wherein the percentage of cassic acid in the mixture is between 0.1% and 1.0% w/w of the mixture, the percentage of L-Arginine is between 47% and 73% w/w of the mixture, and the percentage of undecylenic acid in the mixture is between 26% and 53% w/w of the mixture, further wherein the mixture is combined with an excipient, diluent, or carrier and the concentration of cassic acid in the composition is 0.1 mg/ml or greater.

Also described herein are anti-pathogenic therapeutic compositions configured to be effective to destroy and/or inactivate a virus. For example, an anti-pathogenic therapeutic composition may include a mixture of L-Arginine, undecylenic acid and cassic acid, wherein the percentage of cassic acid in the mixture is between 0.03% and 2.3% w/w of the mixture, the percentage of L-Arginine is between 47% and 73% w/w of the mixture, and the percentage of undecylenic acid in the mixture is between 26% and 53% w/w of the mixture, further wherein the mixture is combined with an excipient, diluent, or carrier. The composition may include any of the components described above (though in some cases may be used at a much higher dilution).

Also described are methods of treating a patient to destroy a virus using an anti-pathogenic agent, the method may include: administering to said patient, a therapeutically effective amount of the anti-pathogenic agent, the anti-pathogenic agent comprising a mixture of L-Arginine, undecylenic acid and cassic acid, wherein the percentage of cassic acid in the mixture is between 0.03% and 2.3% w/w of the mixture, the percentage of L-Arginine is between 47% and 73% w/w of the mixture, and the percentage of undecylenic acid in the mixture is between 26% and about 53% w/w of the mixture, further wherein the mixture is combined with an excipient, diluent, or carrier.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 13 is an example of a 2D gel analysis on a strain of MRSA (untreated).

FIG. 14 is an example of a 2D gel analysis on a strain of MRSA that is treated with an example of an anti-pathogenic composition as described herein.

FIG. 15A-15B show a comparison between the activity of the example anti-pathogenic compound WT13-13 on healthy human cells treated with an anti-pathogenic composition as described herein (HEK293 kidney cells, FIG. 15A) and on untreated bacterial cells (human isolated MRSA cells, FIG. 15B).

DETAILED DESCRIPTION

Figure 1:
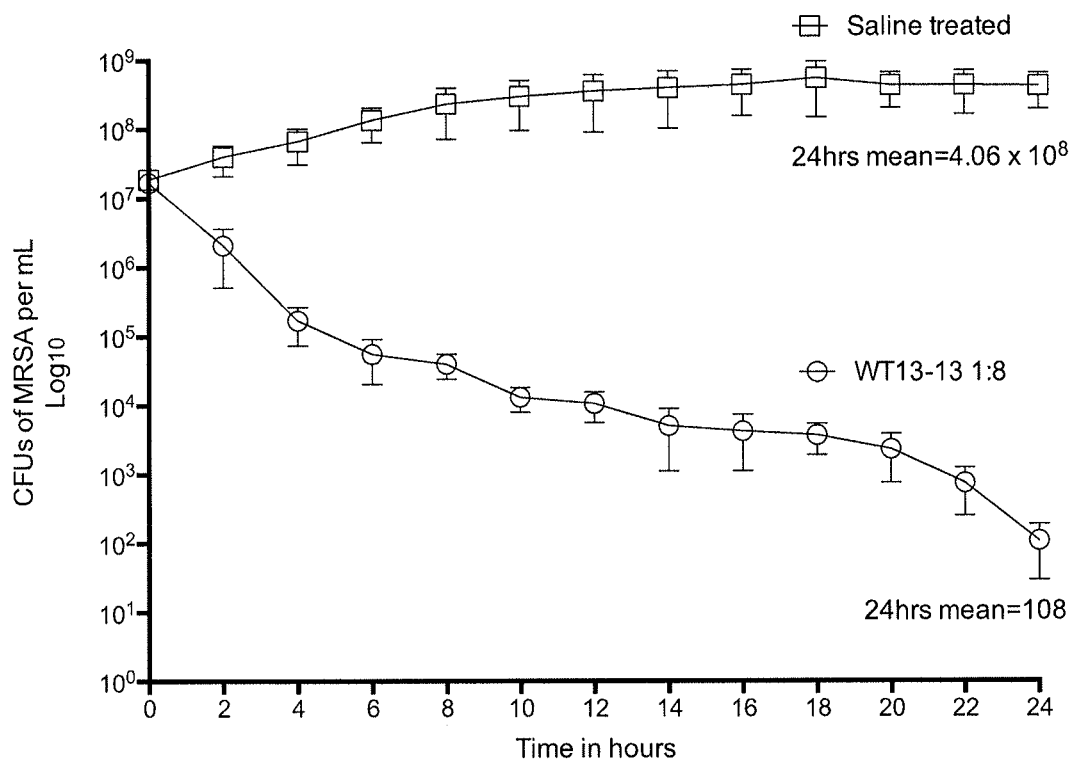
FIG. 1 is a graph showing the minimum bactericidal concentration for one example of an anti-pathogenic therapeutic composition effective against gram negative and gram positive bacteria described herein (referred to as WT13-13). Using an average initial inoculum of $1.6 \times 10^7$ CFUs/mL per microwell, thirty-five (35) MRSA clinical isolates were tested. A 1:8 dilution of WT13-13 provided a minimum bactericidal concentration in 35 samples. At 24 hours, all samples were removed and washed in 400 uL of $diH_2O$ to remove all WT13-13 compound. Samples were then resuspended, plated, and colony count was performed 24 hours after plating. The mean colony count at 24 hours at a 1:8 dilution was 21.6 CFUs. This represents a 99.999% reduction from the starting concentration of $1.6 \times 10^7$ CFUs/mL. Saline treated samples had a final mean value $4.06 \times 10^8$ CFUs/mL. In contrast, WT13-13 treated wells had a mean colony count of $10^8$ CFUs/mL. This represents a 3,703,703 fold reduction in MRSA growth. Error bars represent standard deviations.

Described herein are anti-pathogenic (e.g., antibacterial and/or antiviral and/or antifungal and/or antimicrobial) compounds and methods of using them. The compounds and methods of making and using them described herein are based, in part, on the discovery of mixtures of one or more polar amino acids, one or more anthraquinones and one or more C11 fatty acids to form a mixture having specific ranges of ratios or percentages of each component of the mixture. When the components are within the desired ranges in the mixture, the composition exhibits broad anti-pathogenic therapeutic properties spanning both gram positive (including acid fast gram positive bacteria, such as mycobacteria) and gram negative bacteria, as well as certain pathogenic fungi and viruses. Surprisingly, outside of these defined ranges the anti-pathogenic activity is significantly lost, particularly with respect to certain categories of pathogens, including in particular gram negative bacteria.

These compositions may be used to directly treat a patient (e.g., human or non-human animals) exposed or potentially exposed to a pathogen, to sanitize surfaces, including medical surfaces, as a coating for a medical device or implant, or in any other use in which an anti-pathogenic material would be useful. The compositions described herein also appear to have little direct negative effect on patients (e.g., toxicity).

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

As used herein, the terms below have the meanings indicated.

The term "acyl" as used herein, alone or in combination, refers to a carbonyl attached to an alkenyl, alkyl, aryl, cycloalkyl, heteroaryl, heterocyclyl, or any other moiety where the atom attached to the carbonyl is carbon. An "acetyl" group refers to a —C(O)CH3 group.

An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl" as used herein, alone or in combination, refers to a straight-chain or branched-chain hydrocarbon radical having one or more double bonds optionally substituted and containing from 2 to 20, preferably 2 to 6, carbon atoms. Alkenyl refers to a carbon-carbon double bond system attached at two or more positions such as ethenylene [(—CH=CH—), (—C:C—)]. Examples of alkenyl radicals include ethenyl, propenyl, 2-methylpropenyl, 1,4-butadienyl and the like.

The term "alkoxy" as used herein, alone or in combination, refers to an alkyl ether radical, optionally substituted wherein the term alkyl is as defined below. Examples of alkyl ether radicals include methoxy, ethoxy, n-propoxy, isopropoxy, n-butoxy, iso-butoxy, sec-butoxy, tert-butoxy, and the like.

The term "alkyl" as used herein, alone or in combination, refers to a straight-chain or branched-chain alkyl radical optionally substituted containing from 1 to 20 and including 20, preferably 1 to 10, and more preferably 1 to 6, carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, nonyl and the like.

The term "alkylamino" as used herein, alone or in combination, refers to an alkyl group optionally substituted attached to the parent molecular moiety through an amino group.

Alkylamino groups may be mono- or dialkylated, forming groups such as, for example, N-methylamino, N-ethylamino, N,N-dimethylamino, N,N-ethylmethylamino and the like.

The term "alkylthio" as used herein, alone or in combination, refers to an alkyl thioether (R—S—) radical wherein the term alkyl is as defined above and wherein the sulfur may be singly or doubly oxidized. Examples of alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl" as used herein, alone or in combination, refers to a straight-chain or branched chain hydrocarbon radical having one or more triple bonds and containing from 2 to 20, preferably from 2 to 6, more preferably from 2 to 4, carbon atoms. "Alkynyl" refers to a carbon-carbon triple bond attached at two positions such as ethynylene (—C:C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like.

The term "amido" as used herein, alone or in combination, refer to an amino group as described below attached to the parent molecular moiety through a carbonyl group, or vice versa.

The term "amino" as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted.

The term "aryl" as used herein, alone or in combination, means a carbocyclic aromatic system containing one, two or three rings wherein such rings may be attached together in a pendent manner or may be fused optionally substituted with at least one halogen, an alkyl containing from 1 to 3 carbon atoms, an alkoxyl, an aryl radical, a nitro function, a polyether radical, a heteroaryl radical, a benzoyl radical, an alkyl ester group, a carboxylic acid, a hydroxyl optionally protected with an acetyl or benzoyl group, or an amino function optionally protected with an acetyl or benzoyl group or optionally substituted with at least one alkyl containing from 1 to 12 carbon atoms.

The terms "arylalkyl" or "aralkyl" as used herein, alone or in combination, refers to an aryl group attached to the parent molecular moiety through an alkyl group.

The term "aryloxy" as used herein, alone or in combination, refers to an aryl group attached to the parent molecular moiety through an oxygen atom.

The term "polyether radical" means a polyether radical containing from 2 to 6 carbon atoms interrupted with at least one oxygen atom, such as methoxymethyl, ethoxymethyl or methoxyethoxymethyl radicals or methoxyethyl.

The terms "benzo" and "benz" as used herein, alone or in combination, refer to the divalent radical C6H4=derived from benzene. Examples include benzothiophene and benzimidazole.

The terms "carbamate" and "carbamoyl" as used herein, alone or in combination, refers to an ester of carbamic acid (—NHCOO—) which may be attached to the parent molecular moiety from either the nitrogen or acid end, and which may be optionally substituted as defined herein.

The term "carbonyl" as used herein, when alone includes formyl [—C(O)H] and in combination is a —C(O)— group.

The term "carboxy" as used herein, refers to —C(O)OH or the corresponding "carboxylate" anion, such as is in a carboxylic acid salt. An "O carboxy" group refers to a RC(O)O— group, where R is as defined herein. A "C carboxy" group refers to a —C(O)OR groups where R is as defined herein.

The term "chemical stability" according to the invention means that the content exhibits very little variation with respect to the initial content, namely, that the variation in content of active principle at the time T should not be less than 90% to more particularly than 95% of the initial content at T0.

The term "cyano" as used herein, alone or in combination, refers to —CN.

The term "cycloalkyl" or, alternatively, "carbocycle", as used herein, alone or in combination, refers to a saturated or partially saturated monocyclic, bicyclic or tricyclic alkyl radical wherein each cyclic moiety contains from 3 to 12, preferably five to seven, carbon atom ring members and which may optionally be a benzo-fused ring system which is optionally substituted as defined herein. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as decahydonapthalene, octahydronapthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester" as used herein, alone or in combination, refers to a carboxy group bridging two moieties linked at carbon atoms.

The term "ether" as used herein, alone or in combination, refers to an oxygen atom bridging two moieties linked at carbon atoms.

The terms "halo" or "halogen" as used herein, alone or in combination, refers to fluorine, chlorine, bromine, or iodine.

The term "haloalkyl" as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CHF—), difluoromethylene (—CF2-), chloromethylene (—CHCl—) and the like.

The term "heteroalkyl" as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH2-NH—OCH3.

The term "heteroaryl" as used herein, alone or in combination, refers to 3 to 7 membered, preferably 5 to 7 membered, unsaturated heteromonocyclic rings, or fused polycyclic rings in which at least one of the fused rings is unsaturated, wherein at least one atom is selected from the group consisting of O, S, and N. The term also embraces fused polycyclic groups wherein heterocyclic radicals are fused with aryl radicals, wherein heteroaryl radicals are fused with other heteroaryl radicals, or wherein heteroaryl radicals are fused with cycloalkyl radicals. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groupsincludecarbazolyl, benzidolyl, phenanthrolinyl, dibenzofuranyl, acridinyl, phenanthridinyl, xanthenyl and the like.

The terms "heterocycloalkyl" and, interchangeably, "heterocyclyl", as used herein, alone or in combination, each refer to a saturated, partially unsaturated, or fully unsaturated monocyclic, bicyclic, or tricyclic heterocyclic radical containing at least one, preferably 1 to 4, and more preferably 1 to 2 heteroatoms as ring members, wherein each said heteroatom may be independently selected from the group consisting of nitrogen, oxygen, and sulfur, and wherein there are preferably 3 to 8 ring members in each ring, more preferably 3 to 7 ring members in each ring, and most preferably 5 to 6 ring members in each ring. "Heterocycloalkyl" and "heterocyclyl" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Heterocyclyl groups of the invention are exemplified by aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocyclyl groups may be optionally substituted unless specifically prohibited.

The term "hydroxyl" as used herein, alone or in combination, refers to —OH.

The phrase "in the main chain" refers to the longest contiguous or adjacent chain of carbon atoms starting at the point of attachment of a group to the compounds of this invention.

The phrase "linear chain of atoms" refers to the longest straight chain of atoms independently selected from carbon, nitrogen, oxygen and sulfur.

The term "lower" as used herein, alone or in combination, means containing from 1 to and including 6 carbon atoms.

The term "negatively-charged ion" as used herein, refers to any negatively-charged ion or molecule, either inorganic (e.g., Cl—, Br—, I—) or organic (e.g., TsO— (i.e., tosylate)).

The term "nitro" as used herein, alone or in combination, refers to —NO2.

The term "perhaloalkyl" as used herein, alone or in combination, refers to an alkyl group where all of the hydrogen atoms are replaced by halogen atoms.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstitutedsilyl, N3, SH, SCH3, C(O)CH3, CO2CH3, CO2H, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH2CH3), fully substituted (e.g., —CF2CF3), monosubstituted (e.g., —CH2CH2F) or substituted at a level anywhere in-between fully substituted and monosubstituted (e.g., —CH2CF3). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

Asymmetric centers exist in the compounds of the present invention. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

Optical isomers are compounds with the same molecular formula but differ in the direction they rotate plane polarized light. There are two types of optical isomers. The first type of optical isomers are compounds that are mirror images of one another but cannot be superimposed on each other. These isomers are called "enantiomers." The second type of optical isomers are molecules that are not mirror images but each molecule rotates plane polarized light and are considered optically-active. Such molecules are called "diastereoisomers." Diastereoisomers differ not only in the way they rotate plane polarized light, but also their physical properties. The term "optical isomer" comprises more particularly the enantiomers and the diastereoisomers, in pure form or in the form of a mixture.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "imaging agent" as used herein refers to any moiety useful for the detection, tracing, or visualization of a compound of the invention when coupled thereto. Imaging agents include, e.g., an enzyme, a fluorescent label (e.g., fluorescein), a luminescent label, a bioluminescent label, a magnetic label, a metallic particle (e.g., a gold particle), a nanoparticle, an antibody or fragment thereof (e.g., a Fab, Fab', or F(ab')2 molecule), and biotin. An imaging agent can be coupled to a compound of the invention by, for example, a covalent bond, ionic bond, van der Waals interaction or a hydrophobic bond. An imaging agent of the invention can be a radiolabel coupled to a compound of the invention, or a radioisotope incorporated into the chemical structure of a compound of the invention. Methods of detecting such imaging agents include, but are not limited to, positron emission tomography (PET), X-ray computed tomography (CT) and magnetic resonance imaging (MRI).

The phrase "therapeutically effective" is intended to qualify the amount of active ingredients used in the treatment of a disease or disorder. This amount will achieve the goal of reducing or eliminating the disease or disorder.

The term "therapeutically acceptable" refers to those compounds (or salts, esters, prodrugs, tautomers, zwitterionic forms, etc. thereof) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means mammals and non-mammals. Mammals means any member of the mammalian class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "patient" does not denote a particular age or sex.

The term "prodrug" refers to a compound that is made more active in vivo. Certain compounds of the present invention may also exist as prodrugs, as described in Hydrolysis in Drug and Prodrug Metabolism: Chemistry, Biochemistry, and Enzymology, Testa, Bernard and Wiley-VHCA, Zurich, Switzerland 2003. Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bio-available by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug is a compound that is administered as an ester (the "prodrug"), but then is metabolically hydrolyzed to the carboxylic acid, the active entity. Additional examples include peptidyl derivatives of a compound.

The compounds of the invention can exist as therapeutically acceptable salts. The present invention includes compounds listed above in the form of salts, in particular acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Stahl, P. Heinrich, Pharmaceutical Salts: Properties, Selection, and Use, Wiley-VCHA, Zurich, Switzerland (2002).

The term "therapeutically acceptable salt" as used herein, represents salts or zwitterionic forms of the compounds of the present invention which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trifluoroacetate, trifluoroacetate, phosphate, glutamate, bicarbonate, para-toluenesulfonate (p-tosylate), and undecanoate. Also, basic groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds of the compounds of the present invention and the like.

Compositions

The compositions and therapies described herein may be used to effectively kill and/or inhibit pathogens. Specifically, the compositions may kill or inhibit bacterial growth, and may, at the same time, aid in wound healing. The compositions described herein (anti-pathogenitc compositions) may contain therapeutically-effective amounts of one or more polar amino acids, one or more C11 fatty acids, and one or more anthraquinones. The combination of these compounds may exert a synergistic, not additive, biological mechanism of action that aids in wound healing by causing inhibition of bacterial cell growth and/or bacterial death. Furthermore, the compositions described herein may confer greater therapeutic benefit to a treated patient (e.g., a human) than the sequential administration of the substituent compounds.

The compositions and therapies described herein may be useful for treating symptoms, conditions, and diseases caused by pathogenic infections in a patient (e.g., a human). Also described herein are pharmaceutical preparations and the medicaments obtained therefrom. The methods and formulations to prepare the compositions described herein are disclosed here and in the Examples.

The combinations of a standard (i.e., canonical) or non-standard (i.e., non-canonical) amino acid (in the D or L isomer), and particularly a polar amino acid, with an anthraquinone, and with an unsaturated or saturated C11 fatty acid to form a mixture produces a rapid, potent bactericidal effect in both gram-positive and gram-negative bacteria. Interestingly, combining just two of the aforementioned elements will produce a bacteriostatic effect in both gram-positive and gram-negative bacteria. The proportion of these mixture components (e.g., polar amino acid, anthraquinone and C11 fatty acid) within the mixture may be optimized for the anti-pathogenic effect.

As used herein, an anti-pathogenic material includes antibacterial (bactericidal) compositions. A bactericide may be considered as a chemical entity producing a bacterial kill rate that is greater than the rate of bacterial growth over time, whereas a bacteriostat may be considered as a chemical entity that inhibits bacterial reproduction but does not directly kill the bacteria.

In general, unsaturated fatty acids include, but are not limited to, crotonic acid (CAS Registry Number 107-93-7), myristoleic acid (CAS Registry Number 544-64-9), palmitoleic acid (CAS Registry Number 373-49-9), sapienic acid (CAS Registry Number 17004-51-2), elaidic acid (CAS Registry Number 112-79-8), vaccenic acid (CAS Registry Number 506-17-2), gadoleic acid (CAS Registry Number 29204-02-2), eicosenoic acid (CAS Registry Number 5561-99-9), erucic acid (CAS Registry Number 112-86-7), nervonic acid (CAS Registry Number 506-37-6), linoleic acid (CAS Registry Number 60-33-3, 463-40-1), pinolenic acid (CAS Registry Number 16833-54-8), eleostearic acid (PubChem #5281115), mead acid (CAS Registry Number 20590-32-3), dihomo-gama-linolenic acid (CAS Registry Number 1783-84-2), eicosatrienoic acid (CAS Registry Number 17046-59-2), stearidonic acid (CAS Registry Number 20290-75-9), arachidonic acid (CAS Registry Number 506-32-1), eicosatetraenoic acid (PubChem #231), adrenic acid (CAS Registry Number 28874-58-0), bosseopentaenoic acid (CAS Registry Number 133205-91-1), eicosapentaenoic acid (CAS Registry Number 10417-94-4), ozubondo acid (CAS Registry Number 25182-74-5), tetracosanolpentaenoic acid, docosahexaenoic acid (CAS Registry Number 6217-54-5), and oleic acid (CAS Registry Number 112-80-1).

Saturated fatty acids include, but are not limited to, propanoic acid (CAS Registry Number 79-09-04), butanoic acid (CAS Registry Number 107-92-6), pentanoic acid (CAS Registry Number 109-52-4), hexanoic acid (CAS Registry Number 142-62-1), heptanoic acid (CAS Registry Number 111-14-8), octanoic acid (CAS Registry Number 124-07-2), nonanoic acid (CAS Registry Number 112-05-0), decanoic acid (CAS Registry Number 334-48-5), undecanoic acid (CAS Registry Number 112-37-8), dodecanoic acid (CAS Registry Number 143-07-7), tridecanoic acid (CAS Registry Number 638-53-9), tetradecanoic acid (CAS Registry Number 544-63-8), pentadecanoic acid (CAS Registry Number 1002-84-2), hexadecanoic acid (CAS Registry Number 57-10-3), heptadecanoic acid (CAS Registry Number 506-12-7), octadecanoic acid (CAS Registry Number 57-11-4), nonadecanoic acid (CAS Registry Number 646-30-0), eicosanoic acid (CAS Registry Number 506-30-9), heneicosanoic acid (CAS Registry Number 2363-71-5), docosanoic acid (CAS Registry Number 112-85-6), tricosanoic acid (PubChem #17085), tetracosanoic acid (CAS Registry Number 557-59-5), pentacosanoic acid (PubChem

10468), hexacosanoic acid (CAS Registry Number 506-46-7), heptacosanoic acid (PubChem #23524), octacosanoic acid (CAS Registry Number 506-48-9), nonacosanoic acid (PubChem #20245), triacontanoic acid (CAS Registry Number 506-50-3), henatriacontanoic acid (CAS Registry Number 28232-01-8), dotriacontanoic acid (CAS Registry Number 3625-52-3), tritriacontanoic acid (CAS Registry Number 38232-03-0), tetratriacontanoic acid (CAS Registry Number 506-50-3), pentatriacontanoic acid (PubChem #5282595), hexatriacontanoic acid (CAS Registry Number 4299-38-1), and heptatriacontanoic acid (PubChem #5282597).

As mentioned above, the particular fatty acids of interest herein are C11 fatty acids, such as undecylenic acid. The C11 fatty acids include molecules that include the eleven carbons similar to undecylenic acid and may be combined with other moieties, particular without deleteriously impacting the molecules ability to encapsulate the anthraquinone and polar amino acid.

An anthraquinone (anthracenedione; dioxoanthracene) is defined as an aromatic organic compound with a 9,10-dioxoanthracene core and their corresponding glycosides. Anthraquinones include, but are not limited to, the following compounds and their corresponding glycosides: rhein (i.e., cassic acid; CAS Registry Number 478-43-3), emodin (CAS Registry Number 518-82-1), aloe-emodin (CAS Registry Number 481-72-1), chrysophanol (CAS Registry Number 481-74-3), physcion (CAS Registry Number 521-61-9), dantron (CAS Registry Number 117-10-2), cascarin, catenarin (CAS Registry Number 476-46-0), and diacerein (CAS Registry Number 13739-02-01).

A standard (canonical) or non-standard (non-canonical) amino acid is defined as: an organic compound containing an amine (—NH2) and a carboxyl (—COOH) functional group along with a side chain (R group) specific to each amino acid. This includes proteinogenic and non-proteinogenic amino acids. This includes both D and L isomers (enantiomers). To include the following amino acids in both the D and L isomers, but not limited to: alanine arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, selenocysteine, and pyrrolysine. Polar amino acids are of particular interest herein. Polar amino acids include: arginine, asparagine, aspartate, glutamate, glutamine, and lysine in either L or R chirality (less polar amino acids may include: alanine, glycine, histidine, tyrosine, threonine, serine and proline).

One exemplary composition described herein is referred to as "WT 13-13" and includes a mixture of cassic acid (rhein), undecylenic acid, and L-arginine, in which the relative proportion of these mixture components are within ranges (which may be measured by percent (w/v) of the component in the mixture) that have been found to be effective against a variety of pathogens, including both gram positive and gram negative bacteria, viruses and some fungi. Although WT 13-13 is one example of a composition, other similar compositions may be used, and have also been found to be effective, in particular at providing anti-bacterial effect in both gram-positive and gram-negative bacteria. Furthermore, in repeated exposure studies, drug-resistant bacteria have been unable to develop resistance to the compositions described herein of which WT13-13 is one, non-limiting example.

The mechanism of action of the compositions described herein, including WT13-13 is not yet fully understood. Although possible mechanisms of actions are described herein, it should be understood that these mechanisms are speculative, and a fuller understanding may be elucidated later. However, it is clear that these compositions, and the methods of making and using them are effective even in the absence of a fully elucidated mechanism of action. Thus, the methods and compositions described herein are not limited to a particular mechanism of action.

Because, as shown and discussed in relation to FIG. 22 (described in greater detail below), all three components (e.g., a polar amino acid such as L-Arg, a C11 fatty acid such as UCA, and an anthraquinone such as cassic acid) are necessary to achieve the broad antimicrobial (anti-pathogenic) effects, we hypothesize that the mechanism for these effects are likely to be linked to all three components, likely interacting on separate cellular targets within pathogens (e.g., bacteria) to produce a rapid pathogen-killing effect. Furthermore, each component may be necessary to exert the full (e.g., bactericidal) effect, both in vivo and in vitro. For example, together, each component may produce an effect that combines synergistically and results in an effect that is not present in the individual components. For example, it appears that the effect requires entering the outer layer (wall, membrane, etc.) of the pathogen to allow the anthraquinone to access the nuclear material of the pathogen. One reason for this hypothesis is based on the effect that compositions such as WT13-13 have on the protein expression within the pathogen. For example, FIGS. 13A-13B illustrate an exemplary two-dimensional gel analysis of protein expression, showing treatment with WT13-13 produced a significant reduction in global protein expression within one hour.

L-arginine may be used as some or all of the polar amino acids used in the compositions described herein. The combination of the naturally occurring non-essential amino acid L-arginine with an anthraquinone and a C11 fatty acid has been found to exhibit a profound antimicrobial effect. It is hypothesized that L-arginine (L-Arg) may act as a precursor for the production of nitric oxide (NO). Previous research has shown that NO inhibits the growth of bacteria in vitro. The antimicrobial effect is linked to the production of reactive nitrogen species formed by the oxidation of NO. An example of this is the generation of peroxynitrite (OONO—) resulting from a reaction between NO and the free radical superoxide (O2—). Also, the reaction between NO and thiol groups produces bactericidal nitrosothiols. These reactive nitrogen intermediates destroy the activity of key microbial enzymes, such as aconitase and ribonucleotide reductase by reacting with iron containing groups in these enzymes.

Evidence for this effect is found in the enhanced success of the USA300 CA-MRSA strain. The increased fitness and survivability of this strain has been linked to acquisition of the arginine catabolic mobile element (ACME) from *S. epidermidis*. The primary genetic element of ACME responsible for the increased virulence is linked to the enzyme arginine deiminase. Arginine deiminase catalyzes the formation of L-citrulline from L-arginine and water leading to a reduction in the amount of L-arginine available. This, in turn, reduces the amount of NO produced. Supporting the importance of this mechanism is a recent study in which L-arginine destabilized the development of oral biofilms created by multiple bacterial species.

The inventors have further found that L-arginine, in significant concentrations (as defined herein), may exhibit a potent antimicrobial effect by damaging the bacterial cell membrane (i.e., lysis) by promoting an alkaline environment within the bacterial cell wall and/or viral capsid leading to dysregulated osmotic pressure and the denaturation of key structural proteins. This is supported by data indicating that WT13-13 ruptures the cell well; L-arginine may exert a significant portion of this effect. This effect may allow the other components, e.g., undecylenic acid or cassic acid, to penetrate the bacteria and act upon their respective targets within the pathogen.

L-arginine, as a component in certain compositions of the invention, may also interfere with the formation, repair and structural integrity of peptidoglycan, a common element in both gram-positive and gram-negative bacteria. This occurs when excessive L-arginine is integrated into the peptidoglycan in place of L-alanine, D-glutamine, L-lysine or D-alanine. This in turn weakens the peptidoglycan layer leading to osmotic instability that is further exacerbated by the presence of excessive amounts of basic (alkaline) L-arginine in the cell.

Finally, L-arginine may reduce in vivo bacterial infection by increasing the rate of wound healing. This wound healing is the direct result of enhanced nitric oxide signaling an immune response to the damaged area. This reduces the ability of bacteria to actively infect the lower layers of the dermis. In terms of skin and wound infection, the inventors have previously shown L-arginine to improve wound healing (U.S. Patent Application Publication No. 2015/0366925, hereby incorporated by reference in its entirety).

The anti-pathogenic compositions described herein may also include cassic acid as all or part of the anthraquinone. The inventors have found that cassic acid (also known as rhein), a lipophilic anthraquinone, may exhibit a profound antimicrobial effect by suppressing genes responsible for anaerobic respiration and fermentation, including genes that enable bacteria to utilize nitrate and nitrite as an alternative electron acceptor for metabolism. Further, cassic acid may exert an antibacterial effect via inhibition of the critical topoisomerase IIa (topo IV), intercalation of DNA and the formation of free radicals leading to bacterial, viral, and/or fungal death. Cassic acid also increases the transcription of genes (srtB) encoding iron-regulated surface determinants and genes (nrdIEF and nrdDG) involved in ribonucleotide reductase systems needed to catalyze the formation of deoxyribonucleotides from ribonucleotides. This directly affects the ability of bacteria to manipulate DNA and produce proteins. This effect is readily evident in a two-dimensional gel analysis in which protein expression is globally decreased after one hour of treatment with WT13-13.

Conversely, cassic acid prevents the transcription of genes (pflAB, nirBDR, narGH, ldh1, COL-SA0660, COL-SA2363, and COL-SA2386) responsible for anaerobic respiration and fermentation. Cassic acid has a high binding affinity for CpG DNA. Since bacterial DNA/CpG DNA is a key molecule necessary for the progression of sepsis, subsequently blocking CpG DNA from binding to its receptor decreases the ability of the bacteria to produce protein necessary for survival.

At the cellular level, cassic acid appears to induce a form of prokaryotic apoptosis by stimulating ClpP leading to RecA upregulation responsible for DNA fragmentation. RecA is pivotal in apoptosis of bacteria. Also, cassic acid stimulates the ClpXP complex and the SOS stress response Regulon, both of which trigger apoptosis. These three proteins, stimulated by cassic acid interact to bring about physiological changes when the bacteria experiences stress. The ClpXP protein acts as a regulator of RecA and had been shown to reshape cellular proteomes after DNA damage. The study revealed that these three proteins will act together to change the cell's action when the cell is too stressed by regulating the function of target proteins that are involved in the apoptotic pathway.

Cassic acid may help compromise pathogen viability by modulating DNA synthesis, protein synthesis, and stimulate bacterial apoptosis.

The composition described herein may also include undecylenic acid (UCA) as the C11 fatty acid. In an alkaline environment, UCA spontaneously forms vesicles that may actively encapsulate cassic acid and L-arginine. As a result, encapsulation of the hydrophobic cassic acid by undecylenic acid makes entry into the bacteria, virus, and/or fungal cell wall possible. Furthermore, the L-arginine, once encapsulated, serves to buffer the inner pH of the vesicle and maintain vesicle structure. Once the UCA vesicle has bound to the cell wall of the microorganism, the cassic acid and L-arginine are delivered into the cell or capsid. The UCA then remains part of the cell wall, which leads to structural instability and eventually cell membrane blebbing and disintegration. In particular, UCA as a medium/long chain fatty acid may be incorporated into the cell well, directly interfering with wall teichoic acids (WTAs). WTAs are phosphate-rich, sugar-based polymers attached to the cell walls of bacteria. These anionic polymers serve to reduce osmotic stress as well as regulate cell division, mediate host colonization, and protect enzymatically susceptible peptidoglycan bonds. In the present invention, UCA delivers cassic acid and L-arginine into the cell and then proceeds to destabilize the cell wall. This effect disrupts a wide array of critical, structural, membrane structures in bacteria, viruses and/or fungi that fatally compromise integrity and viability. This may lead to the division and passage of faulty cell walls to progeny cells that have inherent instability due to the incorporation of UCA into membrane lipid structures. Evidence for this effect is found in the exposure experiments detailed herein in which bacterial viability decreased with successive exposures.

In addition to the mixture of amino acids, fatty acids and anthraquinones, one or more additives, such as an excipient, diluent, or carrier (including water), may be used. For example, one or more additives may be used to modify or improve the cosmetic qualities of the final product. For example, one or more further substances with a physiological cooling effect can be used as a component in a mixture according to the invention, and may be selected here from the following list: menthol and menthol derivatives (for example L-menthol, D-menthol, racemic menthol, isomenthol, neoisomenthol, neomenthol) menthylethers (for example (1-menthoxy)-1,2-propandiol, (1-menthoxy)-2-methyl-1,2-propandiol, 1-menthyl-methylether), menthylesters (for example menthylformiate, menthylacetate, menthylisobutyrate, menthyllactates, L-menthyl-L-lactate, L-menthyl-D-lactate, menthyl-(2-methoxy)acetate, menthyl-(2-methoxyethoxy)acetate, menthylpyroglutamate), menthylcarbonates (for example menthylpropyleneglycolcarbonate, menthylethyleneglycolcarbonate, menthytglycerolcarbonate or mixtures thereof), the semi-esters of menthols with a dicarboxylic acid or derivatives thereof (for example mono-menthylsuccinate, mono-menthylglutarate, mono-menthylmalonate, O-menthyl succinic acid ester-N, N-(dimethyl)amide, O-menthyl succinic acid ester amide), menthanecarboxylic acid amides (in this case preferably menthanecarboxylic acid-N-ethylamide [WS3] or N.sup.alpha.-(menthanecarbonyl)glycinethylester [WS5], as described in U.S. Pat. No. 4,150,052, menthanecarboxylic acid-N-(4-cyanophenyl)amide or menthanecarboxylic acid-N-(4-cyanomethylphenyl)amide as described in WO 2005/049553, methanecarboxylic add-N-(alkoxyalkyl)amides), menthone and menthone derivatives (for example L-menthone glycerol ketal), 2,3-dimethyl-2-(2-propyl)-butyric acid derivatives (for example 2,3-dimethyl-2-(2-propyl)-butyric add-N-methylamide [WS23]), isopulegol or its esters (I-(–)-isopulegol, I-(–)-isopulegolacetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840).

Alternatively, the combination therapies of the invention can include additives which cause a hot, sharp, tingly or prickly feeling on the skin or on the mucous membranes, in particular flavors with a heat-producing effect and/or sharp tasting compounds (sharp substances), as described in WO 2005/123101.

Compound Formulation and Administration

Basic addition salts can be prepared during the final isolation and purification of the compounds by reaction of a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid. The novel compounds described herein can be prepared in a form of pharmaceutically acceptable salts that will be prepared from nontoxic inorganic or organic bases including but not limited to aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally-occurring substituted amines, cyclic amines, and basic ion exchange resins, such as arginine, betaine, caffeine, choline, ethylamine, 2-diethylaminoethano, 1,2-dimethylaminoethanol, ethanolamine, ethylenediamine, N-ethyl-morpholine, N-ethylpiperidine, glucamine, glucosamine, histidine, hydroxylamine, isopropylamine, lysine, methylglucamine, morpholine, piperazine, piperidine, polyamine resins, procaine, purines, theobromine, triethylamine, trimethylamine, trishydroxylmethyl amino methane, tripropyl amine, and tromethamine.

If the compounds of the invention are basic, salts could be prepared in a form of pharmaceutically acceptable salts that will be prepared from nontoxic inorganic or organic acids including but not limited to hydrochloric, hydrobromic, phosphoric, sulfuric, tartaric, citric, acetic, fumaric, alkylsulphonic, naphthalenesulphonic, para-toluenesulphonic, camphoric acids, benzenesulfonic, benzoic, camphorsulfonic, citric, ethanesulfonic, gluconic, glutamic, isethonic, lactic, maleic, malic, mandelic, methanesulfonic, mucic, nitric, pamoic, pantothenic, phosphoric, and succinic.

While it may be possible for the compounds of the invention to be administered as the raw chemical, it is also possible to present them as a pharmaceutical formulation. Accordingly, the present invention provides a pharmaceutical formulation comprising a compound or a pharmaceutically acceptable salt, ester, prodrug or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions of the present invention may be manufactured in a manner that is itself known, e.g., by means of conventional mixing, dissolving, granulating, dragee-making, levigating, emulsifying, encapsulating, entrapping or compression processes.

Formulations that may be suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. When used in the diagnostic imaging methods of the invention, the compounds of the invention are preferably administered to the patient (e.g., a human) by intravenous injection. The formulations may conveniently be presented in unit dosage form and may be prepared by any of the methods well known in the art of pharmacy. All methods include the step of bringing into association a compound of the present invention or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds described herein (e.g., anti-pathogenic compounds) may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

In addition to the compounds described herein (e.g., anti-pathogenic compounds) formulations described previously, the compounds of the invention may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compounds described herein (e.g., anti-pathogenic compounds) may take the form of tablets, lozenges, pastilles, or gels formulated in conventional manner. Such compositions may comprise the active ingredient in a flavored basis such as sucrose and acacia or tragacanth.

The compounds described herein (e.g., anti-pathogenic compounds) may also be formulated in rectal compositions such as suppositories or retention enemas, e.g., containing conventional suppository bases such as cocoa butter, polyethylene glycol, or other glycerides.

The compounds described herein (e.g., anti-pathogenic compounds) may be administered topically, that is by non-systemic administration. This includes the application of a compound externally to the epidermis or the buccal cavity and the instillation of such a compound into the ear, eye and nose, such that the compound does not significantly enter the bloodstream. In contrast, systemic administration refers to oral, intravenous, intraperitoneal and intramuscular administration.

Formulations suitable for topical administration include solid, liquid or semi-liquid preparations suitable for penetration through the skin to the site of infection such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Via the topical route, the pharmaceutical compounds described herein (e.g., anti-pathogenic compounds) may be in the form of liquid or semi liquid such as ointments, or in the form of solid such as powders. It may also be in the form of suspensions such as polymeric microspheres, or polymer patches and hydrogels allowing a controlled release. This topical composition may be in anhydrous form, in aqueous form or in the form of an emulsion. The compounds are used topically at a concentration generally of between 0.001% and 10% by weight and preferably between 0.01% and 1% by weight, relative to the total weight of the composition.

For administration by inhalation, the compounds described herein (e.g., anti-pathogenic compounds) may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations of this invention may include other agents conventional in the art having regard to the type of formulation in question, for example, those suitable for oral administration may include flavoring agents.

The compounds described herein (e.g., anti-pathogenic compounds) may be administered orally or via injection at a dose of from 0.1 to 500 mg/kg per day. The dose range for adult humans is generally from 5 mg to 2 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

Compounds described herein (e.g., anti-pathogenic compounds) can be administered at a daily dose of about 0.001 mg/kg to 100 mg/kg of body weight, in 1 to 3 dosage intakes. Further, compounds can be used systemically, at a concentration generally of between 0.001% and 10% by weight and preferably between 0.01% and 1% by weight, relative to the weight of the composition.

The mixture of polar amino acids, anthraquinones and C11 fatty acids (e.g., L-Arg, cassic acid and UCA) may be collectively or separately considered the active ingredient (or if separately, active ingredients) that may be combined with the carrier materials to produce a single dosage form will vary depending upon the host treated and the particular mode of administration.

The compounds described herein (e.g., anti-pathogenic compounds) can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (e.g., anti-pathogenic compounds), or a pharmaceutically acceptable salt, ester, or prodrug thereof, in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for pain involving administration of one of the compounds described herein, increased therapeutic benefit may result by also providing the patient with another therapeutic agent for pain. In any case, regardless of the disease, disorder or condition being treated, the overall benefit experienced by the patient may simply be additive of the two therapeutic agents or the patient may experience a synergistic benefit.

Specific, non-limiting examples of possible combinations with the anti-pathogenic compounds described herein may include use of the anti-pathogenic compounds together with inert or active compounds, or other drugs including wetting agents, flavor enhancers, preserving agents, stabilizers, humidity regulators, pH regulators, osmotic pressure modifiers, emulsifiers, UV-A and UV-B screening agents, antioxidants, depigmenting agents such as hydroquinone or kojic acid, emollients, moisturizers, for instance glycerol, PEG 400, or urea, antiseborrhoeic or antiacne agents, such as S-carboxymethylcysteine, S-benzylcysteamine, salts thereof or derivatives thereof, or benzoyl peroxide, antibiotics, for instance erythromycin and tetracyclines, chemotherapeutic agent, for example, paclitaxel, antifungal agents such as ketoconazole, agents for promoting regrowth of the hair, for example, minoxidil (2,4-diamino-6-piperidinopyrimidine 3-oxide), non-steroidal anti-inflammatory agents, carotenoids, and especially p-carotene, antipsoriatic agents such as anthralin and its derivatives, eicosa-5,8,11,14-tetraynoic acid and eicosa-5,8,11-triynoic acid, and esters and amides thereof, retinoids, e.g., RAR or RXR receptor ligands, which may be natural or synthetic, corticosteroids or oestrogens, alpha-hydroxy acids and a-keto acids or derivatives thereof, such as lactic acid, malic acid, citric acid, and also the salts, amides or esters thereof, or p-hydroxy acids or derivatives thereof, such as salicylic acid and the salts, amides or esters thereof, ion-channel blockers such as potassium-channel blockers, or alternatively, more particularly for the pharmaceutical compositions, in combination with medicaments known to interfere with the immune system, anticonvulsant agents include, and are not limited to, topiramate, analogs of topiramate, carbamazepine, valproic acid, lamotrigine, gabapentin, phenytoin and the like and mixtures or pharmaceutically acceptable salts thereof. A person skilled in the art will take care to select the other compound(s) to be added to these compositions such that the advantageous properties intrinsically associated with the compounds of the invention are not, or are not substantially, adversely affected by the envisaged addition.

In any case, the multiple therapeutic agents (at least one of which is a compound of the present invention) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, methods for treating diseases, disorders, conditions, or symptoms in a patient (e.g., a human or animal) in need of such treatment are presented herein, the methods comprising the step of administering to the patient an amount of a compound of the invention effective to reduce or prevent the disease, disorder, condition, or symptom, in combination with at least one additional agent for the treatment of said disorder that is known in the art.

Any of the anti-pathogenic compositions described herein may be formulated for coating a surface, including coating surfaces of medical devices to prevent bacteria colonization, biofilm formation and the development of hospital acquired infections. The application of medical devices, including their long term use, can lead to bacterial colonization, biofilm formation, and the development of hospital-acquired bacterial infections, often referred to as nosocomial infections. This includes catheter-related blood stream infection, orthopedic implantations, ventilator associated pneumonia, surgical site infection and catheter associated urinary tract infection. This can result in the need to remove and/or replace the medical device. An anti-pathogenic formulation (e.g., including the polar amino acid, anthraquinone, and C11 fatty acid) may be applied to the surface of a medical device in a number of ways, including ionic binding to a surface, passive adsorption, or embedding the formulation within a polymer matrix. The formulation may be used in combination with other molecules, biofilm matrix degrading substances or other antibacterial agents. Any medical device may be coated as described herein, including, e.g., implantable medical devices (stents, shunts, vasooclusive coils, grafts, pins, plates, etc.) and non-implantable devices (catheters, masks, surgical tools, etc.).

EXAMPLES

Therapeutic compounds described herein (e.g., anti-pathogenic compounds) can be administered in combination with one or more additional agents for the treatment of any of the diseases, disorders, conditions, or symptoms described herein.

It is understood that the foregoing examples are merely illustrative. Certain modifications of the compositions, articles and/or methods employed may be made and still achieve the objectives of the invention. Such modifications are contemplated as within the scope of the claimed invention. In said examples to follow, all parts and percentages are given by weight, unless otherwise indicated.

Example 1. WT13-13 Preparation

One non-limiting example of an anti-pathogentic composition comprising a polar amino acid, and anthraquinone and a C11 fatty acid is described herein, and is referred to as WT13-13. This exemplary composition includes a mixture of L-Arg, cassic acid and UCA in which the mixture includes approximately 62% L-Arg, 37.6% UCA and 0.4% cassic acid. This mixture may be combined with any additive (e.g., excipient, diluent, or carrier, including water) to dilute the mixture, while retaining the relative amounts of the L-Arg, UCA and cassic acid. WT13-13 may be prepared, for example, by:

1. Add 50 g of L-arginine to 100 mL of diH2O and stir/heat at 65-85 degrees Celsius until all L-arginine goes into solution (preventing as much evaporation as possible).

2. Aliquot 100 mL of the diH2O/L-arginine solution into a separate beaker containing 25 mL of undecylenic acid (UCA) and 2.5 G of cetyl alcohol and stir and heat at 65-85 degrees Celsius until the cetyl alcohol and undecylenic acid go completely into solution (preventing as much evaporation as possible).

3. Add 250 mg of cassic acid to the undecylenic acid/L-arginine solution and stir until the cassic acid goes completely into solution (preventing as much evaporation as possible).

In some variations, a composition that does not include any cassic acid (anthraquinone) was formulated similarly. This composition displayed bacteriostatic (slowing the growth) effects on both gram negative and gram positive bacteria. This composition (referred to herein as WT13-13*, may be prepared by:

1. Add 50 g of L-arginine to 100 mL of diH2O and stir/heat at 65-85 degrees Celsius until all L-arginine goes into solution (preventing as much evaporation as possible).

2. Aliquot 100 mL of the diH2O/L-Arginine solution into a separate beaker containing 25 mL of undecylenic acid and 2.5 G of cetyl alcohol and stir and heat at 65-85 degrees Celsius until cetyl alcohol and undecylenic acid go completely into solution (preventing as much evaporation as possible).

Example 2: Minimum Bactericidal Concentration for WT13-13 (FIG. 1)

Using an average initial inoculum of $1.6 \times 10^7$ CFUs/mL of MRSA per microwell, the inventors tested 35 clinically isolated MRSA samples. This is illustrated in FIG. 1. A 1:8 dilution of WT13-13 provided a minimum bactericidal concentration in 35 samples. This represents a 99.999% reduction from the starting concentration of $1.6 \times 10^7$. Saline treated samples had a final mean value $4.06 \times 10^8$ CFUs/mL. In contrast, WT13-13* (not shown) had a mean colony count of 108. This represents a 3,703,703 fold reduction in MRSA. This effect was confirmed by a manual mean colony count at 24 hours in the 1:8 dilution was 21.6 CFUs. Error bars represent standard deviation.

Figure 2:
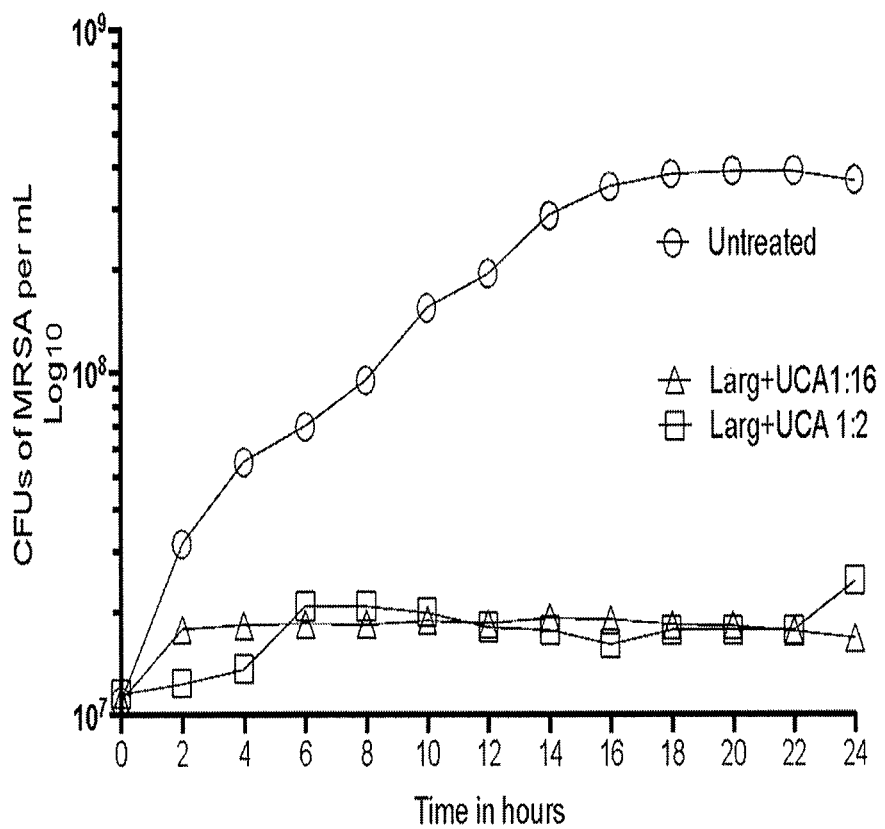
FIG. 2 is a graph showing that a mixture of just L-arginine and undecylenic acid (without an anthraquinone) produce a bacteriostatic effect but are unable to achieve a bactericidal effect in the absence of the anthraquinone. Using an average initial inoculum of $1.1 \times 10^7$ CFUs/mL per microwell, four (4) MRSA clinical isolates were tested. At 1:16 and 1:2 dilutions, L-arginine and undecylenic acid together produce a non-dose dependent bacteriostatic effect.

Example 3: L-Arginine and Undecylenic Acid Produce a Bacteriostatic Effect but are Unable to Achieve a Bactericidal Effect in the Absence of an Anthraquinone As shown in FIG. 2, compositions that omitted the anthraquinone (e.g., WT13-13*) were also tested, but showed bacteriostatic, but not bactericidal, effects. Using an average initial inoculum of $1.1 \times 10^7$ CFUs/mL of MRSA per microwell we tested four (4) clinically isolated MRSA samples. At 1:16 and a 1:2 dilution L-arginine and undecylenic acid combined together produced a non-dose dependent bacteriostatic effect that was significantly less effective than the combination of L-arginine, undecylenic acid, and cassic acid.

Figure 3:
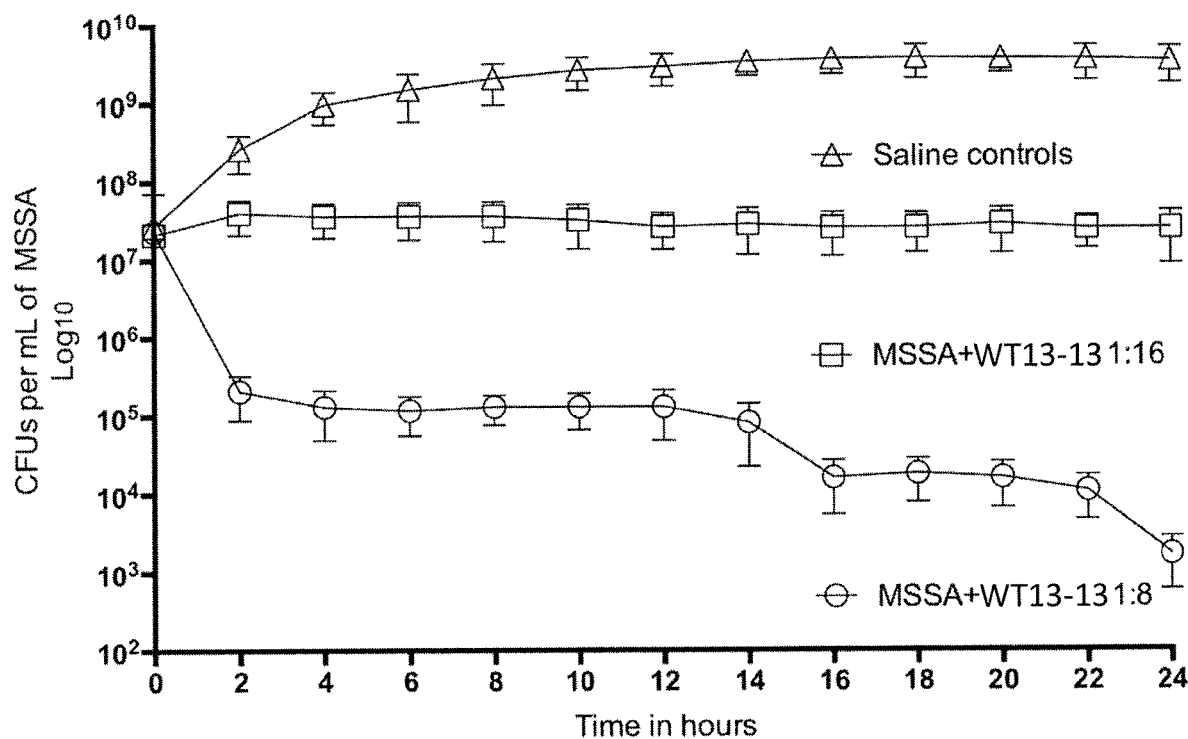
FIG. 3 shows the activity of WT13-13 against human-isolated Methicillin-susceptible *Staphylococcus aureus* (MSSA).

In contrast, anti-pathogenic composition comprising a polar amino acid, and anthraquinone and a C11 fatty acid as described herein, such as WT13-13 described above, showed strongly antibacterial effects for both gram positive and gram negative bacteria. For example, FIG. 3 is a graph illustrating the effect of two dilutions of WT 13-13 prepared as described above on Methicillin-susceptible *Staphylococcus aureus* (MSSA). As shown in FIG. 3, the minimum inhibitory concentration 100 ($MIC_{100}$). Using an average starting concentration of 2.32e7 CFUs per mL of MSSA, the inventors tested 30 clinically isolated samples. Using a dose response dilution series, we determine that a 1:16 dilution of WT13-13 provided a minimum inhibitory concentration in 30 samples. A 1:8 dilution provide an MBC. Error bars show standard deviation. Thus, FIG. 3 shows the activity of WT13-13 against human-isolated MSSA; the minimum bacteriostatic concentration (MBC) is 1:8 (diluted from full strength). The minimum inhibitory concentration (MIC) is 1:16.

Figure 4:
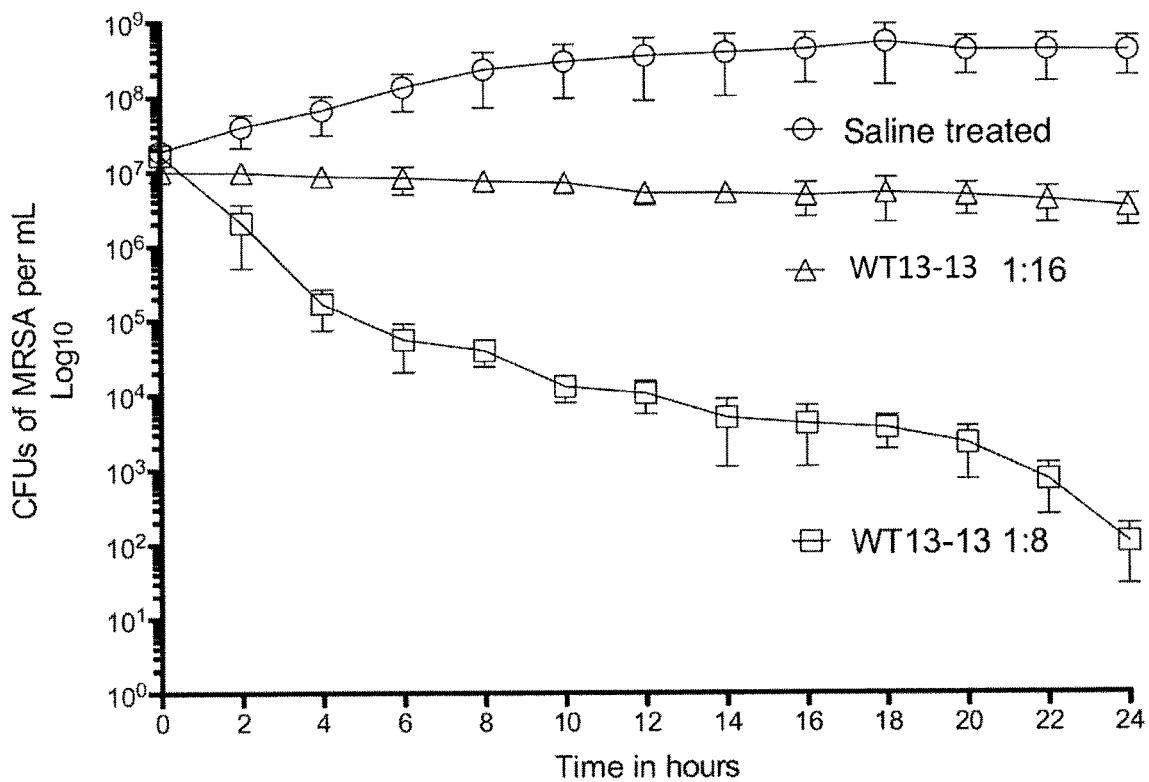
FIG. 4 shows the activity of WT13-13 against human-isolated methicillin-resistant *Staphylococcus aureus* (MRSA).

FIG. 4 shows the activity of WT13-13 against human-isolated methicillin-resistant *Staphylococcus aureus* (MRSA). Using an average initial inoculum of $1.6 \times 10^7$ CFUs/mL of MRSA per microwells, we tested 35 clinically isolated MRSA samples. A 1:8 dilution of WT13-13 provided a minimum bactericidal concentration in 35 samples. This represents a 99.999% reduction from the starting concentration of $1.6 \times 10^7$. Saline treated samples had a final mean value of $4.06 \times 10^8$ CFUs/mL. In contrast, WT 13-13 had a mean colony count of 108. This represents a 3,703,703 fold reduction in MRSA. This effect was confirmed by a manual mean colony count at 24 hours in the 1:8 dilution that was 21.6 CFUs. Error bars represent standard deviation. This, in this example, the MBC is 1:8, and the MIC is 1:16.

Figure 5:
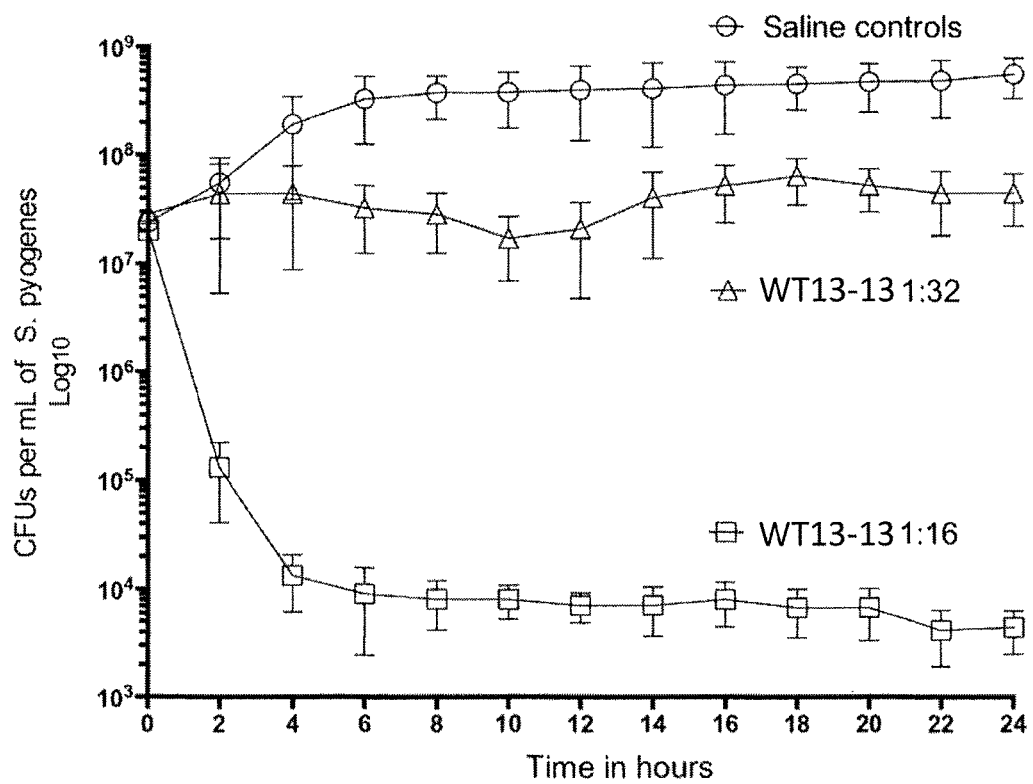
FIG. 5 shows the activity of WT13-13 against human-isolated *S. pypogenes*.

FIG. 5 shows the activity of WT13-13 against human-isolated *S. pypogenes*, following a similar assay to that shown in FIGS. 3 and 4, above. In this example, the MBC is 1:16, and the MIC is 1:32. MIC100 and minimum inhibitor concentration (MBC) for *S. pyogenes* using WT 13-13 was calculated using an average starting concentration of 2.4e7 CFUs per mL of MRSA. 17 clinically isolated samples were tested. Using a dose response dilution series, we determined a 1:32 dilution of WT13-13 that provided a minimum inhibitory concentration in 17 samples. A 1:16 dilution provided the MBC. Error bars represent standard deviation.

Figure 6:
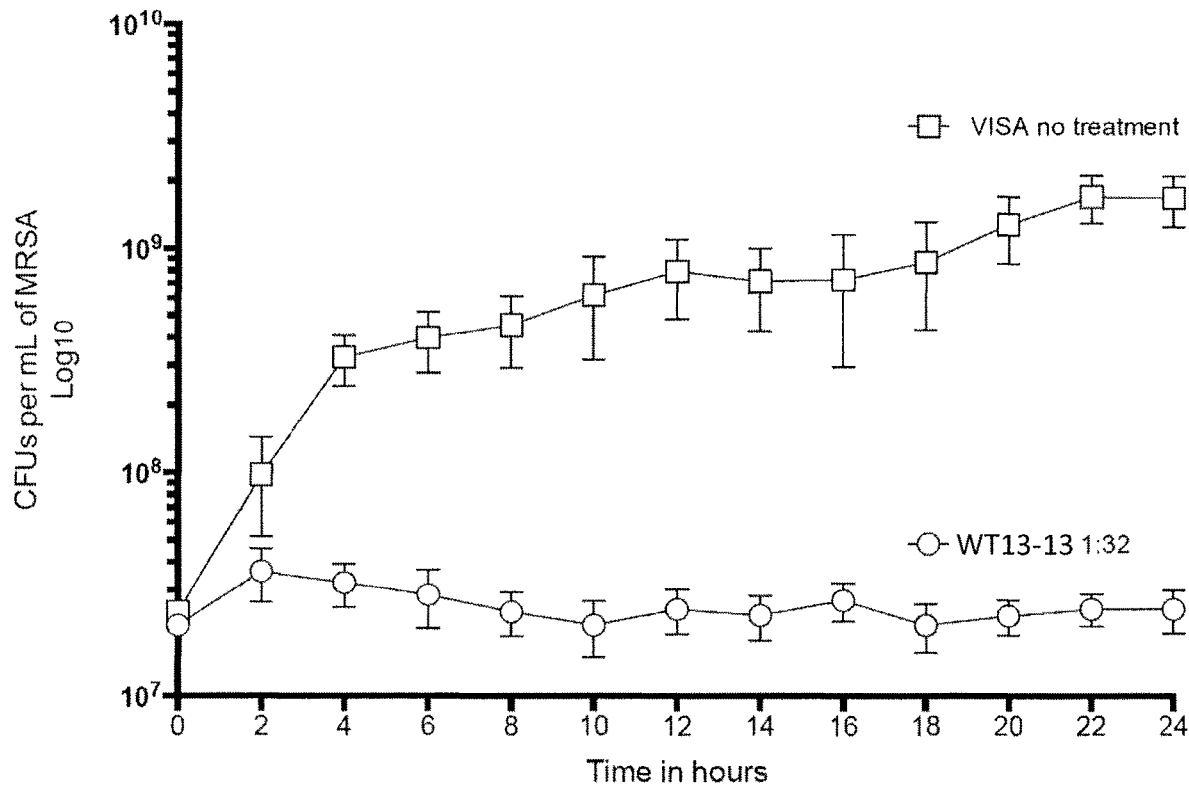
FIG. 6 shows the activity of WT13-13 against human-isolated Vancomycin intermediate *staphylococcus* (VISA).

FIG. 6 shows the activity of WT13-13 against human-isolated Vancomycin intermediate staphylococcus (VISA, used in place of VRSA). As shown, the MIC for this example of an anti-pathogenic compound was 1:32.

Figure 7:
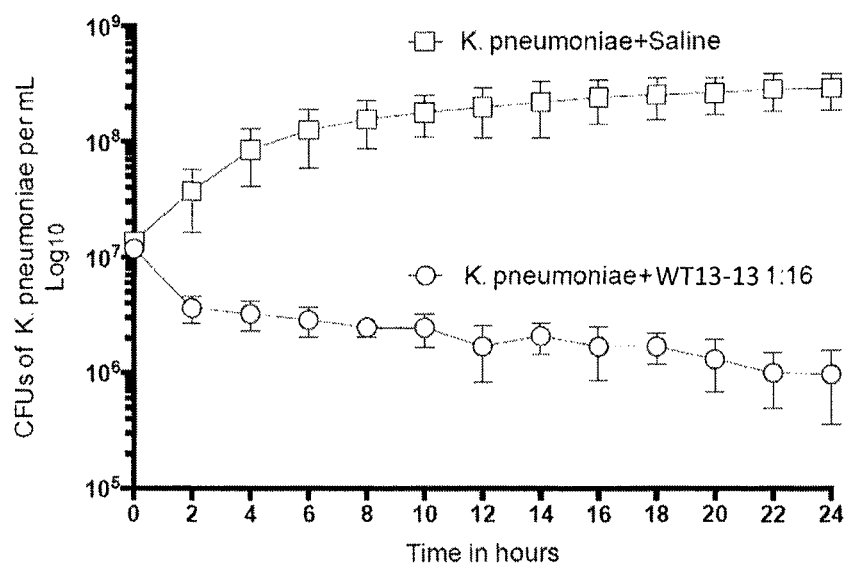
FIG. 7 shows the activity of WT13-13 against human-isolated *Klebsiella pneumoniae* (*K. pneumoniae*).
Figure 8:
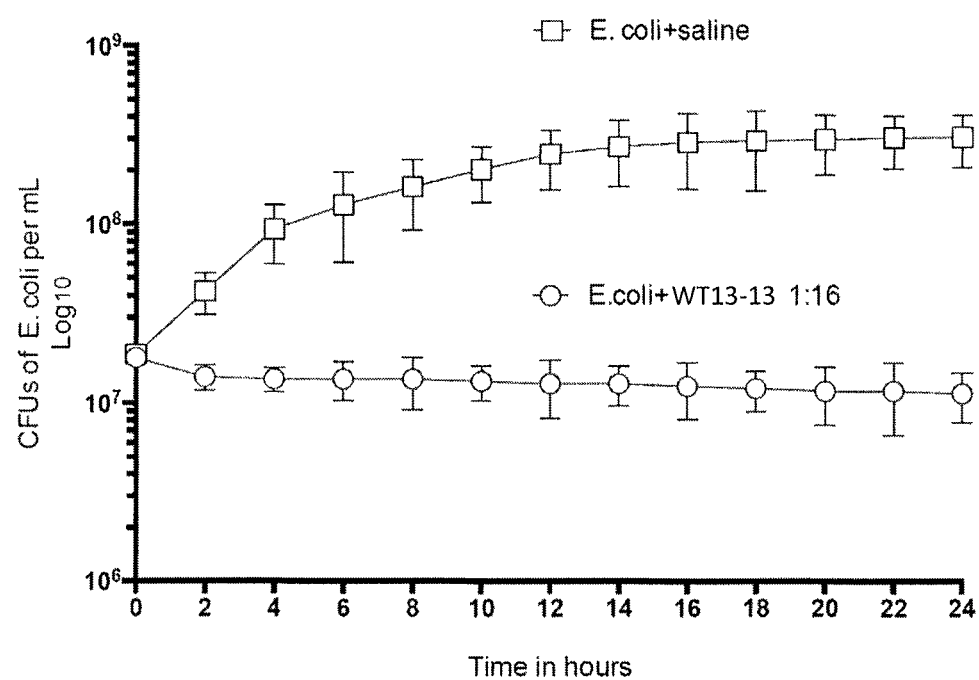
FIG. 8 shows a similar assay against *E. coli* (*Escherichia coli*).

Similarly, FIG. 7 shows the activity of WT13-13 against human-isolated *Klebsiella pneumoniae* (*K. pneumoniae*). In this example, the MIC was found to be 1:16. FIG. 8 shows a similar assay against *E. coli* (*Escherichia coli*). In FIG. 8 the activity of WT13-13 against human-isolated *E. coli* showed a MIC is 1:16 (n=15).

Figure 9:
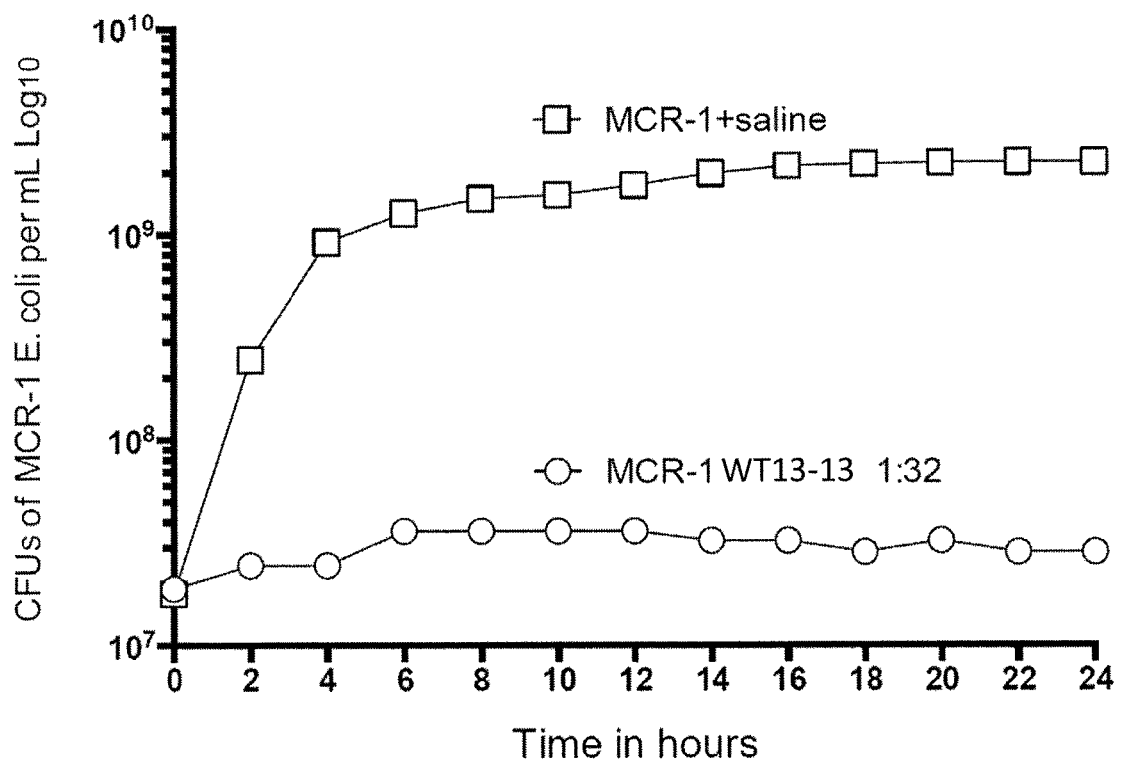
FIG. 9 shows the activity of WT13-13 against human-isolated *E. coli* expressing the MCR-1 gene.

FIG. 9 shows the activity of WT13-13 against human-isolated *E. coli* expressing the MCR-1 gene (n=2). In this example, the MIC was 1:32, despite the presence of the MCR-1 gene. The mobilized colistin resistance (MCR-1) gene confers plasmid-mediated resistance to colistin, one of a number of last-resort antibiotics for treating gram negative infections.

In addition to the examples shown in FIGS. 1-9, other pathogens were examined with both the WT13-13 anti-pathogen compound as well as other anti-pathogen compounds having different percentages of amino acid, anthraquinone, and fatty acid in the mixture (see, e.g., table 1, below), showing similar results, that is anti-pathogenic response. In general, it appears that some ratios of the three components (polar amino acid, C11 fatty acid, and anthraquinone) had particularly robust anti-pathogenic responses. Outside of these ranges, the anti-pathogenic response was less robust, although a bacteriostatic effect may have been seen. For example, the percentage of the polar amino acid (e.g., L-Arg) may be between 47% and 73%, with particularly robust responses expected at about 62%. The percentage of C11 fatty acid (e.g., UCA) may be between 26% and 53%, with particularly robust responses expected at about 37.6%). The percentage of the anthraquinone (e.g., cassic acid) may be between 0.03% and 2.3%, with particularly robust effects expected between 0.1% and 1% (e.g., about 0.4%). At higher percentages of each of these components, but especially the anthraquinone, the composition may have to be adjusted to enhance the solubility of the components.

Figure 10:
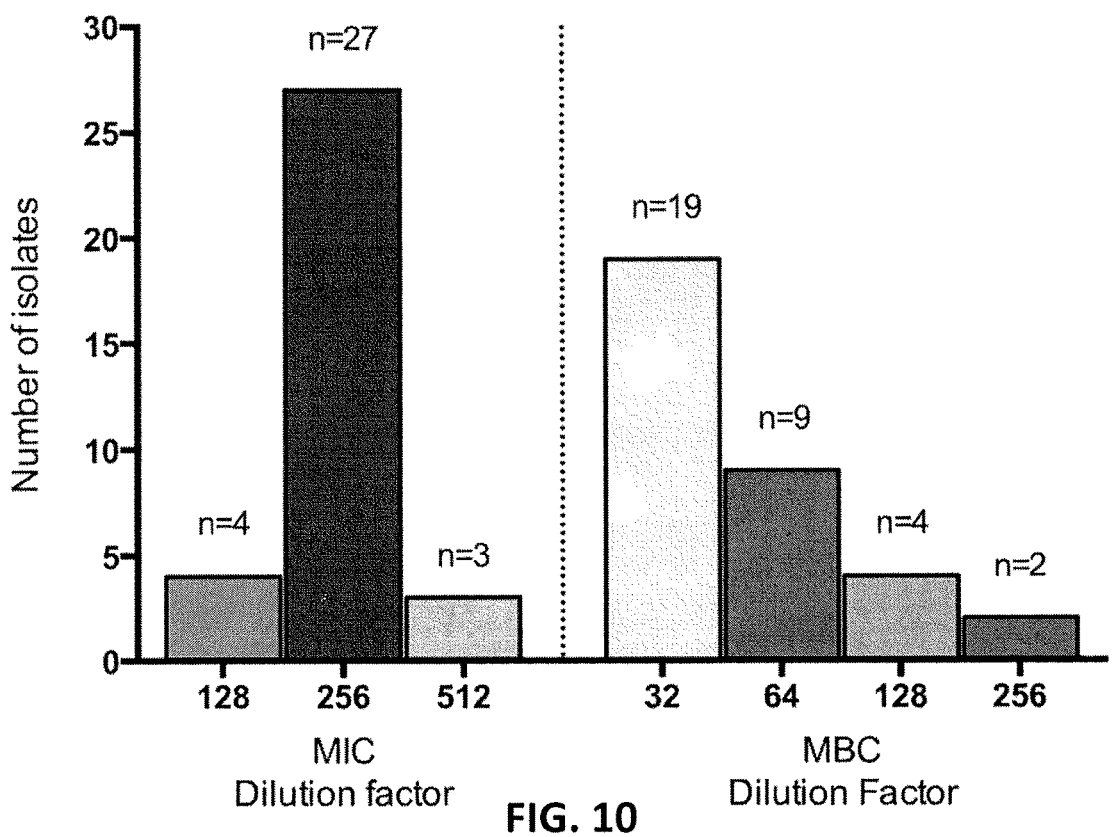
FIG. 10 shows the MIC and MBC for one example of an anti-pathogenic composition described herein.

An independent testing group was used to validate the MIC and MBC data described above. When using the WT13-13 example for testing MRSA, a different testing method was used. For example, MIC was tested using the same clinical isolates but with a resazurin solution. A standardized inoculum of $1.0 \times 10^6$ CFU/mL was utilized in a 96 well format and serially diluted. MBC Testing: Aliquots of a positive control, the MIC value, and five concentrations above the MIC. In FIG. 10, the graph shows an MIC of 1:256. Differences in the MIC dilutions may be attributed to the starting bacterial concentrations. (e.g., $10^6$ CFUs vs. $10^7$ CFUs from the data shown in FIGS. 1-2). In FIG. 10, the MBC was determined to be the concentration of antimicrobial agent, which showed a 99.9% reduction in viable cell growth compared to the negative control.

Figure 11:
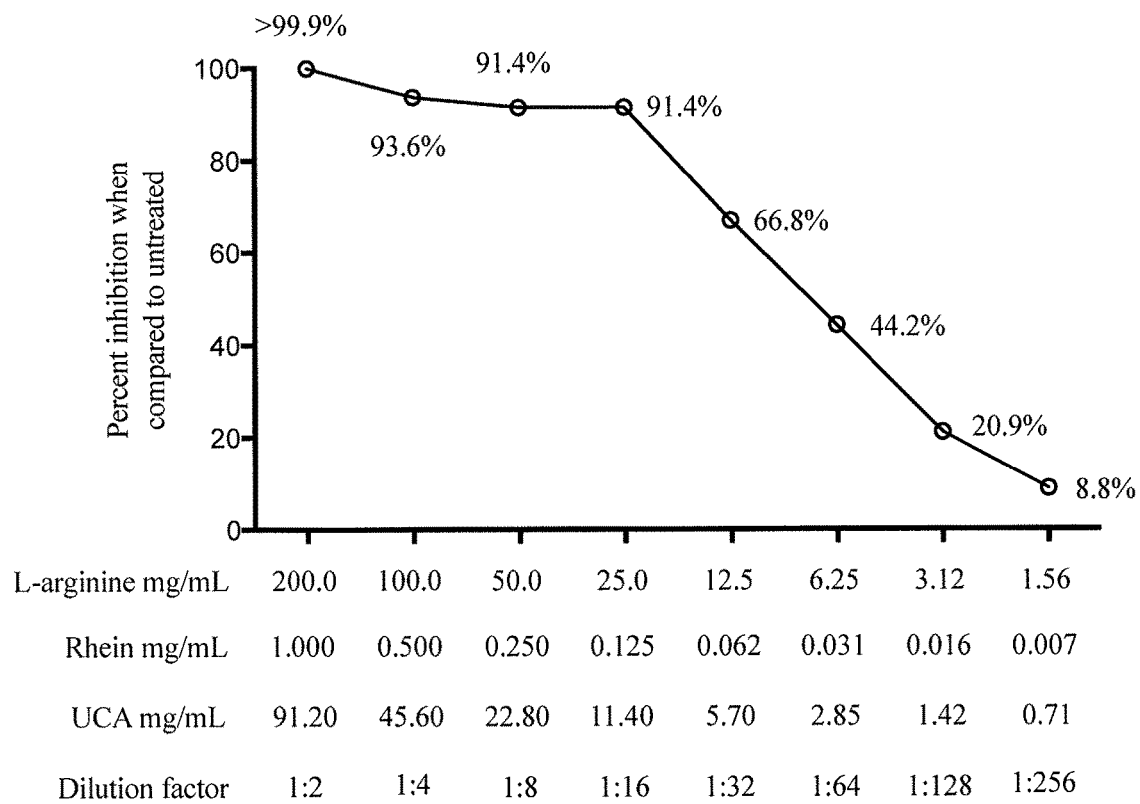
FIG. 11 is a dose-response curve for the antibiotic effect of one exemplary anti-pathogenic composition described herein.

A dose-response study was used to examine the antibiotic effect of the WT13-13 exemplary composition. This is illustrated in FIG. 11. In this example, concentrations ranging from undiluted to 1:128 were tested against the USA 300 strain of MRSA. Using an iodonitrotetrazolium chloride (INT; Sigma-Aldrich) assay, triplicate negative control wells and their blanks, each experimental well was inoculated with MRSA in Luria Broth (LB) containing approximately 100,000 CFUs/well. Blank wells had 100ul, of sterile LB added. After 24 hours of incubation a measurement for each well was taken on a plate reader at 680 nm. The readings were averaged for each of the treatment groups and subtracted by their respective blanks. The resulting numbers were compared to those of the negative controls and a relative efficacy was determined for each treatment group. The numbers are represented in percentages.

Figure 12:
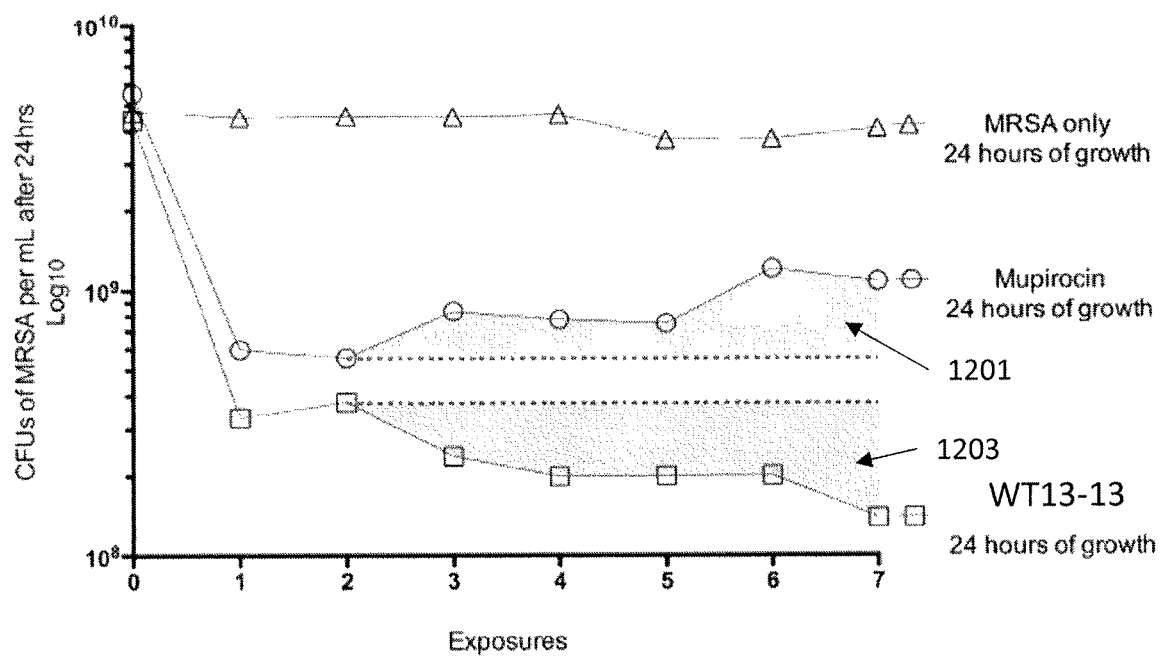
FIG. 12 illustrates a comparison of resistance developed to a known antibiotic (Mupirocin) compared to an example of an anti-pathogenic composition as described herein.

Surprisingly, the anti-pathogenic compounds described generated little or no antibiotic resistance compared to known antibiotics (e.g., mupirocin). A number of standard in-vitro resistance studies were conducted to predict the onset and mechanism of resistance for an anti-pathogenic compound such as WT13-13. The standard test comprises exposing bacteria to sub-inhibitory concentrations of an antibiotic over a number of exposures and monitoring the bacterial growth. As the bacteria develop resistance to the drug, the growth rate will rise. Tests were performed by treating MRSA with sub-inhibitory concentrations of both WT13-13 and mupirocin (separately) in order to study the behavior of WT13-13 and compare with that of mupirocin. The results of this study are shown in FIG. 12. The horizontal dotted lines represent the ideal, non-resistant behavior. That is, if an antibiotic were effective and the bacteria not developing resistance to it, its growth curve would be flat and follow the dotted line. However, all antibiotics to date experience bacterial resistance and trend upwards of the dotted line, towards the MRSA-only control line (if an antibiotic reaches the control line, it is completely ineffective and the bacteria is resistant to the antibiotic). As seen in FIG. 12, mupirocin clearly trends upwards towards the control line, displaying textbook resistance development. The shading 1201 highlights this behavior. In contrast, WT13-13 actually trends downwards, below the dotted line, indicating that bacteria become less viable and more susceptible to WT13-13 over multiple exposures, and does not become resistant to WT13-13. The shading 1203 highlights this behavior. This result was reliably reproduced. Such "anti-resistance" has not been reported in an antibiotic before.

In addition to the above, 2D gel analysis on the USA300 strain of MRSA was performed. Colonies of MRSA were treated with either sterile water or WT13-13 for 1 hour. After treatment, colonies were harvested, processed, protein normalized prior to loading, and run on a 2D gel. Results from this study suggest that treatment with WT13-13 significantly decreases global protein expression in the USA300 strain of MRSA. This is shown in FIG. 13 (showing cells exposed just to vehicle) and FIG. 14 (showing cells exposed to the WT13-13 example compound by 2D gel analysis.

FIGS. 15A-15B shows a comparison between the activity of the example anti-pathogenic compound WT13-13 on healthy human cells (HEK293 kidney cells) and on bacterial cells (human isolated MRSA cells). This standard test comprised exposing each set of cells to the test compound (e.g., WT13-13) for one hour, followed exposure to a fluorescent dye that only binds to broken DNA in dead or dying cells. The healthy human cells exposed to the WT13-13 compound showed no signs of dye uptake and therefore no damage. In contrast, the MRSA cells are highly fluorescent post-exposure to WT13-13, indicating bactericidal activity (as expected).

Figure 16A:
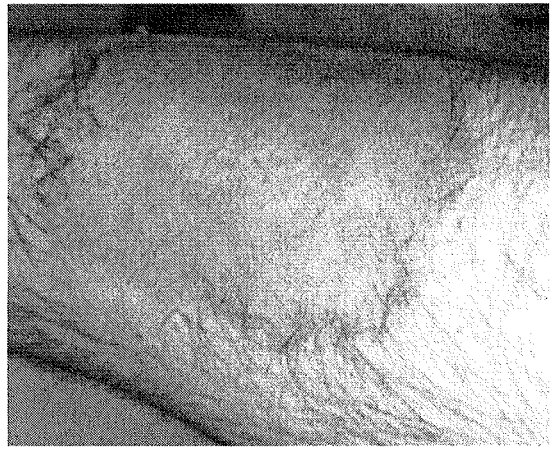
FIGS. 16A-16D show a skin-irritation study using the anti-pathogenic composition as described herein.
Figure 16B:
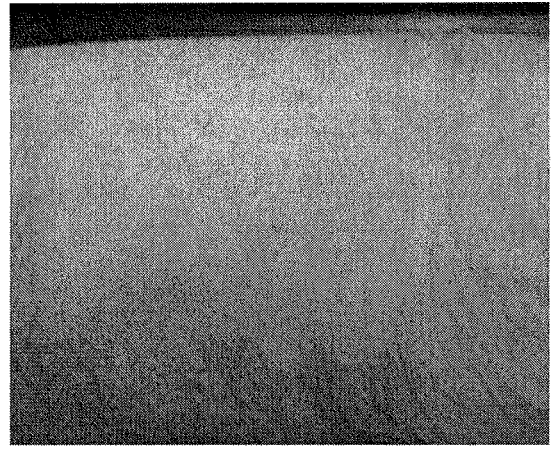
Figure 16C:
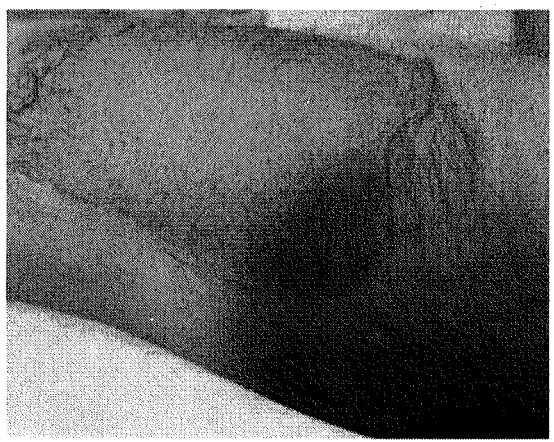
Figure 16D:
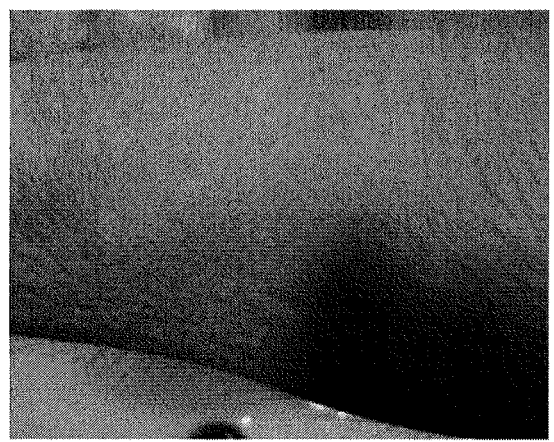

The example anti-pathogenic compounds described herein (e.g., WT 13-13) showed little or no skin irritation when tested on healthy volunteers. As shown in FIGS. 16A-16D, a preliminary skin irritation study was conducted for WT13-13. The study includes the application of WT13-13 to one healthy volunteer once daily for eight days and close observation of the skin immediately after application, and 10 hours post-application. No irritation or sensitization of the skin occurred, and the volunteer did not report any side effects or discomfort. FIG. 16A shows the patient's arm skin with a solution of WT13-13 applied on day 1. The WT13-13 solution results in a reddish color on the skin due to the pigmentation of the solution; this color washes off in water. FIG. 16B shows day 1, after 10 hours post-application; no irritation is present. FIG. 16C shows the same skin region after reapplication at day 8. FIG. 16D shows this region on day 8, 10 hours post-application. More than ten healthy individuals have voluntarily applied WT13-13 in uncontrolled studies. None reported any adverse effects (e.g., no irritation or sensitization of the skin was seen or reported).

Figure 17:
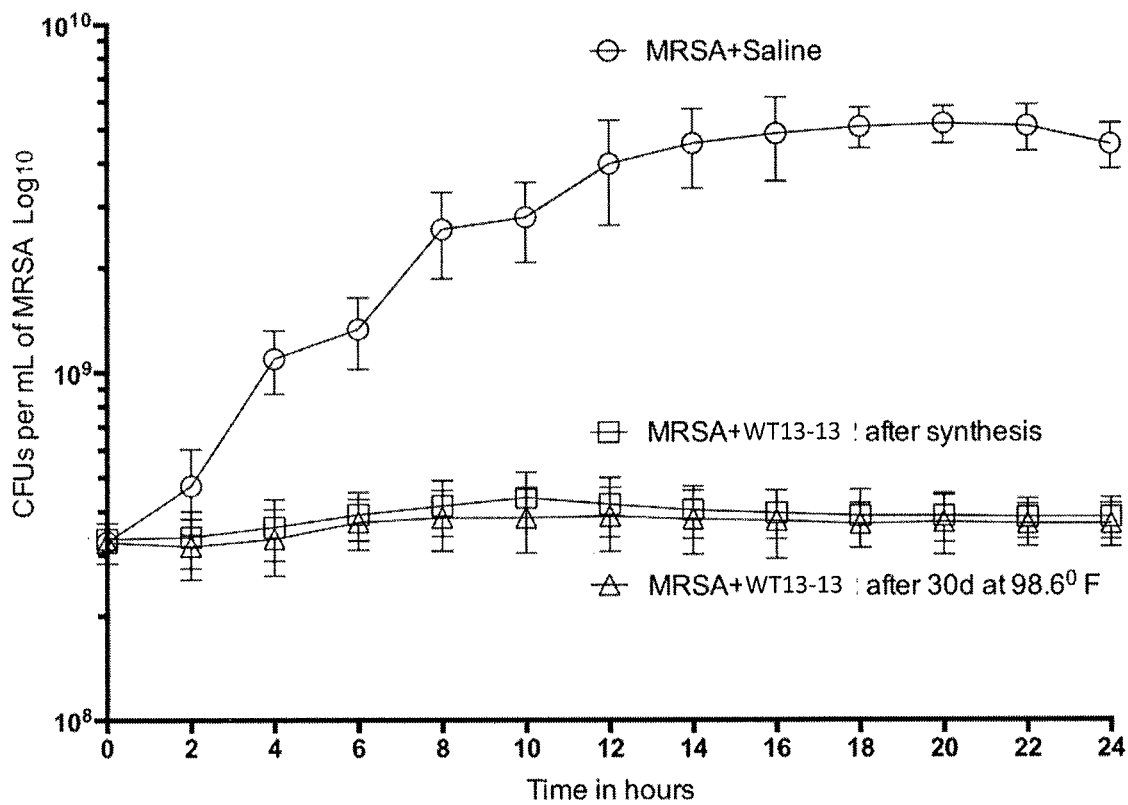
FIG. 17 shows stability testing over time at different temperatures for an anti-pathogenic composition as described herein.
Figure 18:
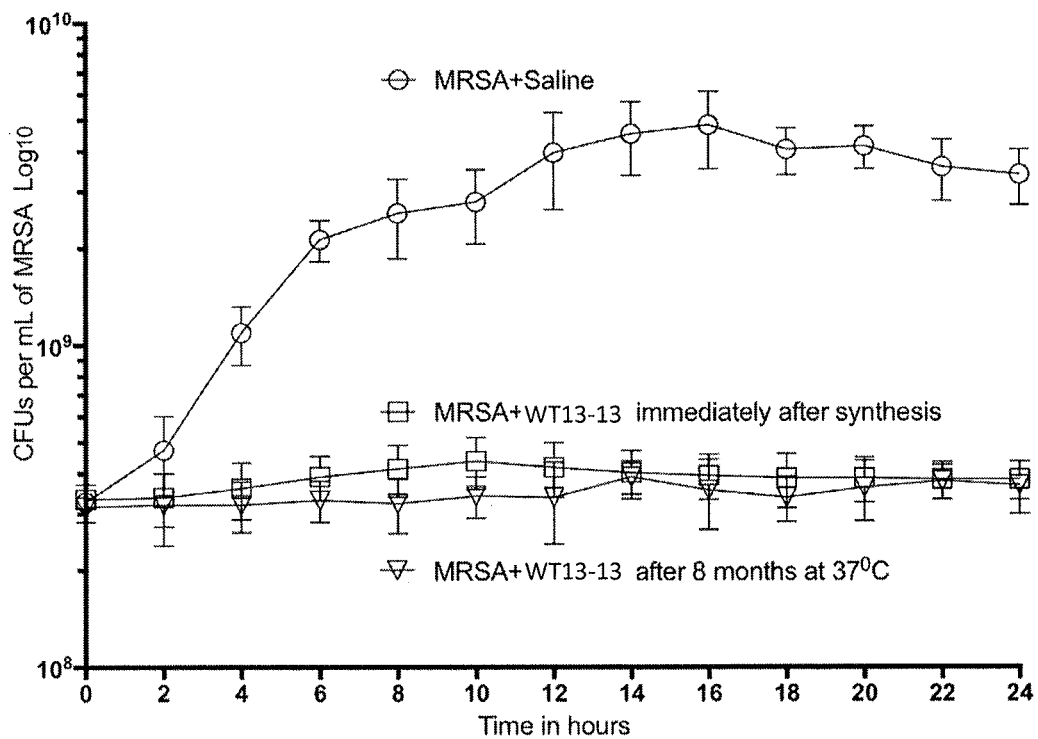
FIG. 18 shows stability testing over time for an anti-pathogenic composition as described herein.

The compositions described herein were also examined for stability. Preliminary stability testing verified the activity of the example anti-pathogenic compound WT13-13 after long shelf times and exposures to temperatures. Data is illustrated in FIGS. 17 and 18. In this example, a fresh batch of WT13-13 was produced and divided into two lots. The first lot was tested immediately, while the second lot was placed on hold at a temperature of 37° C. (99° F.) and then tested for activity at 30 days (results shown in FIG. 17); and 8 months (results shown in FIG. 18). As at both 30 days and 8 months the anti-pathogenic compounds described herein show excellent stability.

Figure 19:
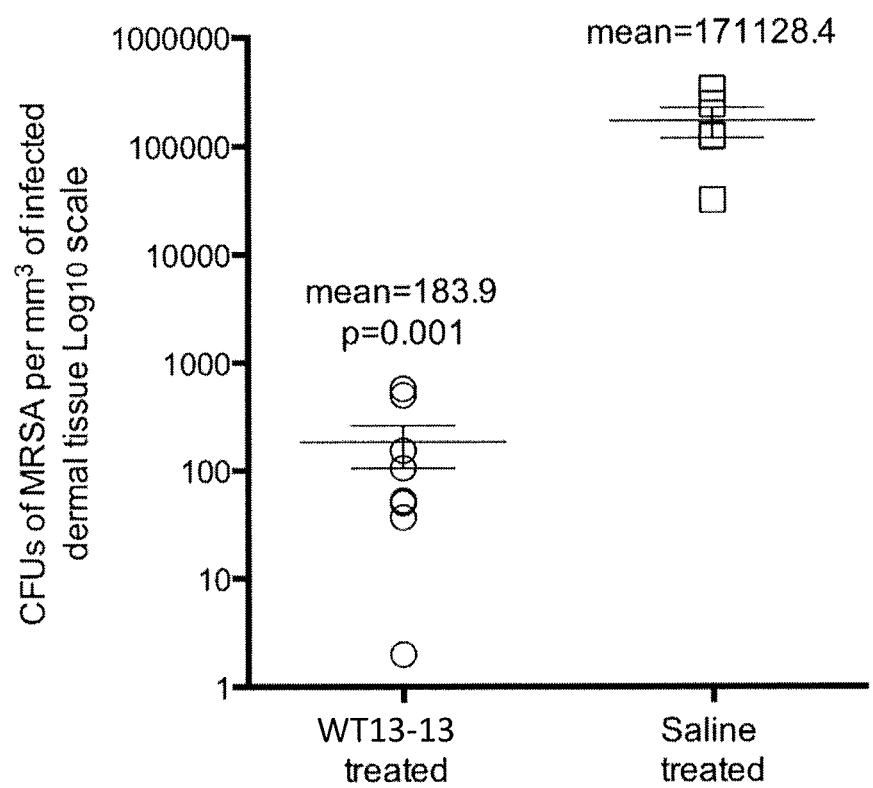
FIG. 19 graphically shows the results of an in vivo skin study using the anti-pathogenic composition as described herein.

In-vivo animal studies for the example anti-pathogenic compound WT13-13 were conducted, including a dermal study. The dermal study was tested WT13-13 on an active MRSA skin infection. The study was conducted using rats. In the dermal study, a dermal abrasion on each animal was infected it with 750,000 CFUs of MRSA. 24 hours after infection, the animals were either treated with undiluted WT13-13 or with saline (control). This was repeated for 7 days. At the end of 7 days, tissue samples were taken and analyzed. Animals treated with WT13-13 had a 99.9% reduction in MRSA organisms present. This modelling is designed to replicate impetigo, mediated by MRSA, in humans. FIG. 19 shows the results of this study. The treated sites were largely free of pathogen, while untreated were highly infected.

The evidence collected to date strongly indicates that the anti-pathogen compounds including a mixture of polar amino acids, C11 fatty acids, and anthraquinones (such as the L-Arg, UCA and cassic acid mixture of WT13-13) within the specified proportions, results in a highly potent, broad-spectrum, non-toxic (safe) antibiotic, with unique "anti-resistance" properties.

Prior work by the inventors (e.g., US 2015/0366925 to Hale) demonstrated an antibiotic effect using a mixture of L-arginine, undecylenic acid and a plant extract from Rheum Officinale. This extract was found to provide antibiotic effect against some classes of bacteria (e.g., gram positive) but not others, including gram negative bacteria. The amount of cassic acid in the extract was determined to be less than 0.0315 mg/mL, compared to previously used L-Arg and UCA concentrations of 100 mg/mL and 182.4 mg/mL, respectively; thus, the percentage of cassic acid is less than 0.01%. Even when accounting for other possible anthraquinones present in the extract, there is a qualitative and unexpected difference in the effect of the anti-pathogenic effects of the compositions (e.g., compounds) described herein, compared to the use of extracts of Rheum Officinale. Surprisingly, the use of extract alone provides a mildly effective antibacterial effect on just gram positive bacteria. In contrast the compositions described herein have a highly potent antibacterial effect on gram positive bacteria, gram negative bacteria, and other pathogens, including viruses and fungi, but only when the relative percentages of the polar amino acids, C11 fatty acids and anthraquinones are within the specified percent ranges of a mixture. For example, if the cassic acid (rhein) is below 0.03%, the composition does not retain the anti-bacterial efficacy. Preliminary analysis suggests that the antibacterial effect of the anti-pathogenic compositions have two to five times, or more, the antibacterial activity on gram positive bacteria when normalized for concentration.

Figure 20:
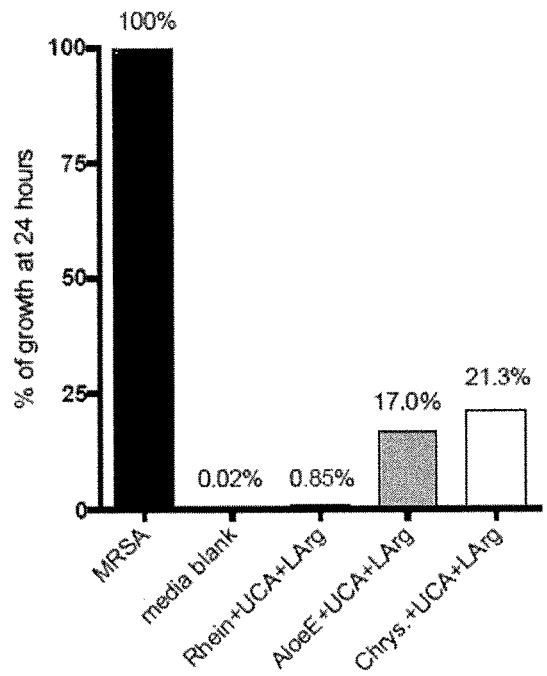
FIG. 20 illustrates the antibiotic effect of various anthraquinones in combination with undecylenic acid and L-arginine.

Although the WT13-13 example compound described herein uses cassic acid (rhein) as the anthraquinones, other anthraquinones may be used. This is illustrated in FIG. 20, for example. In FIG. 20, antibiotic effects of other anthraquinones were tested against MRSA. As shown, identical ratios of L-Arg and UCA were combined with various anthraquinones, including cassic acid (Rhein), aloe-emodin (AloeE), and chrysophanol (Chyrs.). Formulations were tested for MRSA growth using an iodonitrotetrazolium chloride assay. Each compound was MRSA was assayed in media control and subtracted from the values taken from the wells containing MRSA to control for colorimetric alterations. Each MRSA well contained 100,000 CFUs in 100 microliters. Cassie acid (Rhein) was more effective than aloe-emodin (AloeE), and chrysophanol (Chyrs.) in this assay, although the amount of these anthraquinones were less than cassic acid in this preliminary assay.

Figure 21:
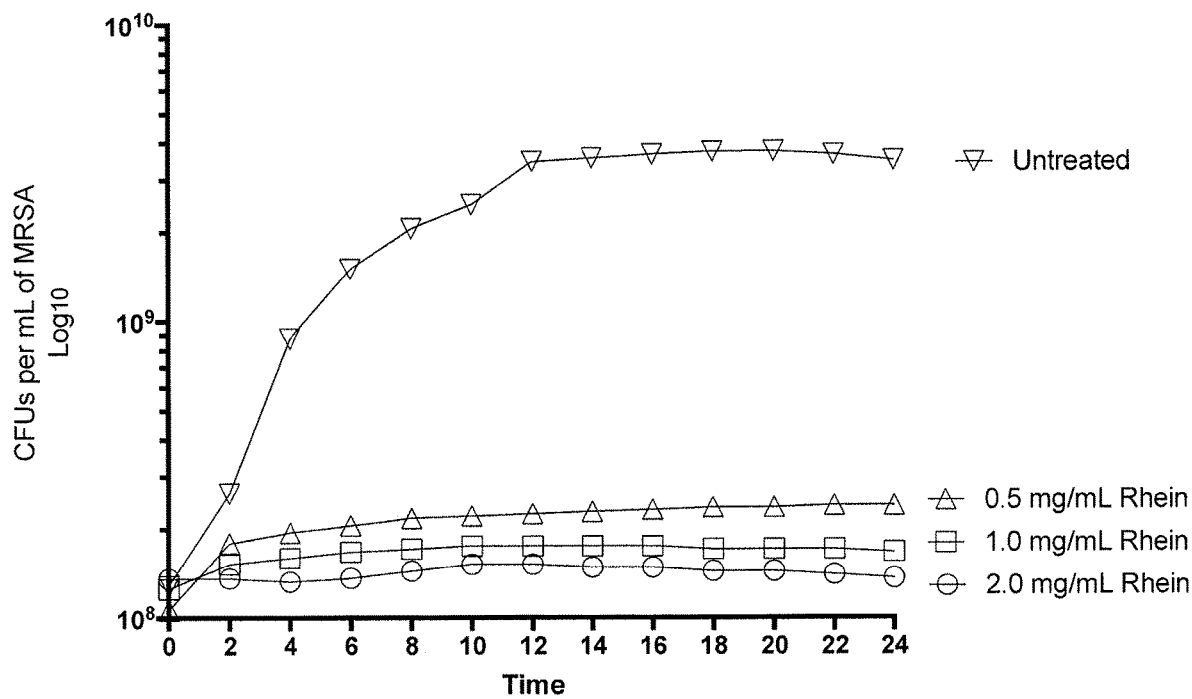
FIG. 21 illustrates the sensitivity of the anti-pathogenic compounds described herein to the proportion of anthraquinone.
Figure 22:
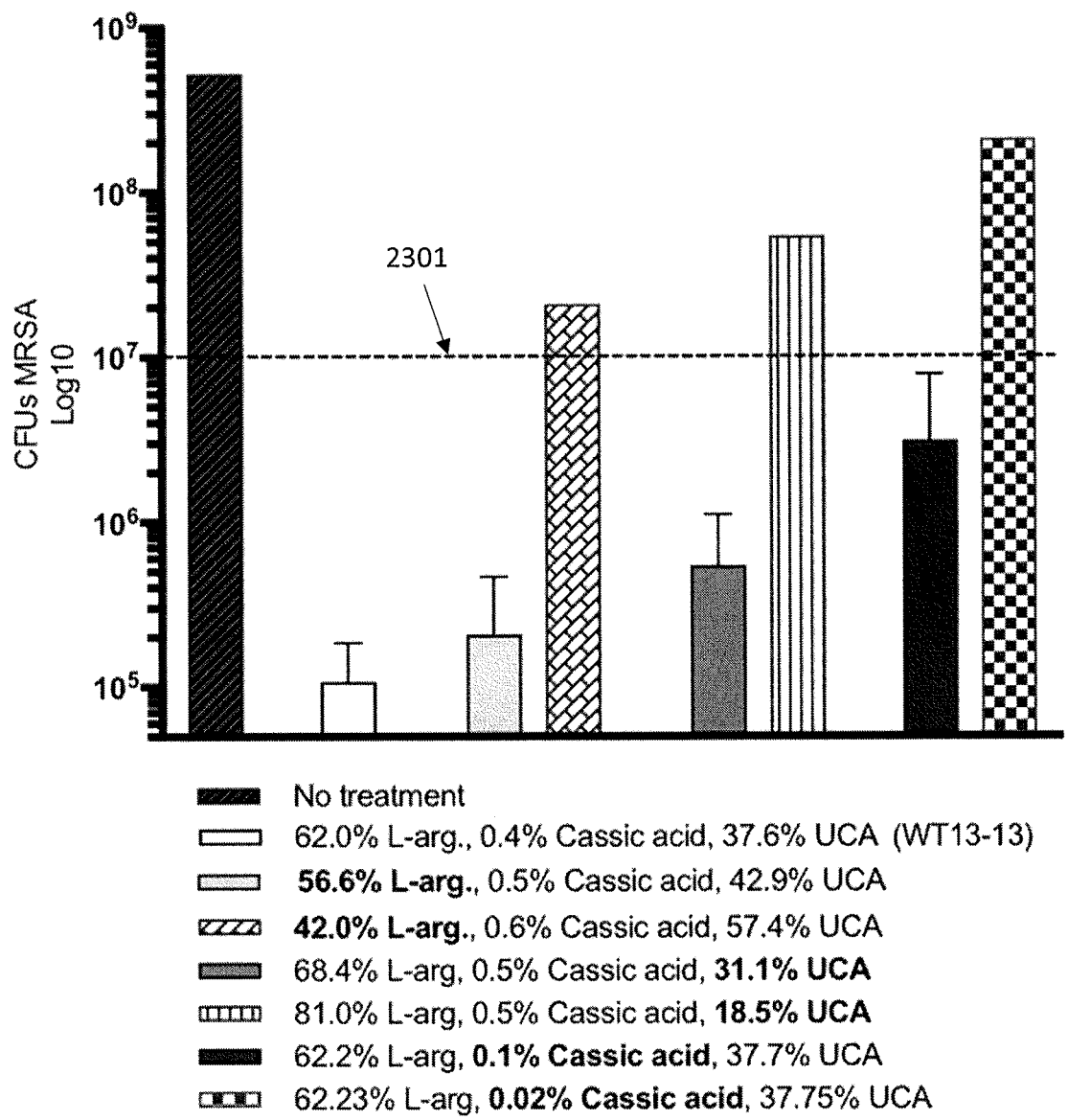
FIG. 22 illustrate the sensitivity of the anti-pathogenic compounds described herein to the proportion of anthraquinone, polar amino acid and C11 fatty acid.

FIGS. 21 and 22 illustrate the sensitivity of the anti-pathogenic compounds described herein to the proportion of anthraquinone, polar amino acid and C11 fatty acid. For example, in FIG. 21, the amount of cassic acid (rhein) was varied relative to the constant amount of L-Arg and UCA. In general, decreasing the relative amount of cassic acid affects the efficacy of the compound against bacteria such as MRSA. In this example, using an average starting concentration of 1.21e8 CFUs/mL, the inventors observed a decreased efficacy against MRSA when cassic acid concentrations were reduced from 2.0 mg/mL (0.34%) by halves (1.0 mg/mL or 0.17%, 0.5 mg/mL or 0.075%). Further dilution of the cassic acid resulted in a substantial loss of antibiotic efficacy, particularly beyond 0.02%-0.03%).

FIG. 22 illustrates the effect of changing the relative percentages of the components of the mixture, e.g., the relative amounts of the polar amino acids (e.g., L-Arg) and C11 fatty acids (e.g., UCA), on the anti-pathogenic effect of the compounds described herein. WT13-13 (far left) shows a high level of antibiotic effect against MRSA. Changing just the relative percent of the L-Arg (e.g., reducing it from 62.0% to 56.6%, and increasing the relative percent of UCA to accommodate this change, as shown in the third bar) results in a decrease in antibacterial efficacy, though the resulting compound still displayed antibacterial effects. Further reduction in the relative L-Arg percentage of the mixture of L-Arg, cassic acid and UCA (bar 4, showing a decrease from 56.4% to 45.0%) is predicted to show a loss of antibacterial effect (prophetic example). Similarly, reducing the relative percentage of UCA in the mixture from 37.6% to 31.1%, shown in bar 5, also results in a decrease in antibacterial activity against MRSA. Further reduction (bar 6, prophetic example) to 18.5% is expected to result in a loss of antibacterial efficacy. The dashed horizontal line 2301 represents the threshold for antibacterial activity (above this line the activity may not be considered antibacterial). These results demonstrate that changes to the relative amounts of these three components of the mixture may decrease the efficacy of against multi-drug resistant bacteria.

In this example, an excipient (cetyl alcohol at 20.0 mg/mL) remained constant across the tests.

As mentioned above, in addition to cassic acid, one or more other anthraquinones may be used with or in place of cassic acid. For example, addition to cassic acid (e.g., rhein), one or more of emodin (e.g., aloe emodin, aloeE), physcion, chrysophanol, dantron, cascarin, catenarin, and/or diacerein are anthraquinones that may be used as part of a mixture with one or more C11 saturated and unsaturated fatty acids (e.g., undecylenic acid), and one or more polar amino acids (e.g., L-Arg) to form an anti-pathogenic therapeutic composition effective against gram negative and gram positive bacteria. In general, these compositions may include a mixture of: one or more polar amino acid (e.g., L-Arginine), one or more C11 saturated and/or unsaturated fatty acid (e.g., undecylenic acid) and one or more anthraquinones (e.g., cassic acid). The percentage of anthraquinones in the mixture may be between about 0.03% and about 2.3% w/w of the mixture (e.g., between about 0.1% and about 1.0%, or more particularly, about 0.4% w/w of the mixture), the percentage of polar amino acid may be between about 47% and about 73% w/w of the mixture (e.g., between 47% and 73% w/w of the mixture, or more particularly, about 62% w/w of the mixture), and the percentage of C11 saturated and/or unsaturated fatty acids may be between about 26% and about 53% w/w of the mixture (e.g., between about 26% and about 53% w/w of the mixture, or more particularly about 37.6% w/w of the mixture). In any of these compounds the mixture may combined with an excipient, diluent, or carrier. For compounds having broad antibacterial effects, the total concentration of anthraquinone in the mixture may be about 0.1 mg/ml or greater (e.g., about 0.15 mg/ml or greater, 0.17 mg/ml or greater, 0.18 mg/ml or greater, 0.2 mg/ml or greater, 0.25 mg/ml or greater, 0.27 mg/ml or greater, 0.3 mg/ml or greater, etc.).

Although in general, the anthraquinones are considered toxic (and are known to cause hepatomyoencephalopathy in children), the mixtures described herein have been found to be anti-pathogenic across a broad number of pathogens (including both gram negative and gram positive bacteria, fungi, and viruses, and in particular those listed in table 1, below, at concentrations that do not affect mammalian cells (see, e.g., FIGS. 15A-15B, discussed above). Thus, compositions may be referred to as anti-pathogenic therapeutic composition effective against gram negative bacteria (or anti-pathogenic therapeutic composition effective against gram negative bacteria and gram positive bacteria); they may also be effective against numerous other pathogens. As illustrated and discussed above in FIGS. 2-10 above, the compounds described herein may be used to treat (e.g., kill and/or stop the growth of) any of the classes of microorganisms, and specifically those listed below in Table 1.

TABLE 1

List of pathogen treatable by the anti-pathogenic compounds

| Micro-organism | Class |
|---|---|
| Carbapenem-resistant Enterobacteriaceae (CRE) | Gram Negative Rod (GNR) |
| Extended spectrum β-lactamase producing Enterobacteriaceae (ESBLs) | GNR |
| Multidrug-resistant *Pseudomonas aeruginosa* | GNR, aerobic Facultative anaerobe |
| Methicillin-resistant *Staphylococcus aureus* (MRSA) | Gram Positive Cocci (GPC) |
| Drug-resistant *Streptococcus pneumoniae* | GPC |
| Vancomycin-resistant *Staphylococcus aureus* (VRSA) | GPC |
| Vancomycin intermediate-resistant *Staphylococcus aureus* (VISA) | GPC |
| Erythromycin-resistant Group A *Streptococcus* | GPC |
| Clindamycin-resistant Group B *Streptococcus* | GPC |
| Methicillin-susceptible *Staphylococcus aureus* (MSSA) | GPC |
| *Streptococcus pyogenes* | GPC |
| Group C *Streptococcus* | GPC - |
| *Enterococcus* (Group D *Streptococcus*) | GPC - |
| *Escherichia coli* | GNR, aerobic Facultative anaerobe |
| *Klebsiella pneumoniae* | GNR, aerobic Facultative anaerobe |
| *Proteus vulgaris* | GNR, aerobic Facultative anaerobe |
| *M. ulcerans* | mycobacteria |
| *Bacteroides fragilis* | GNR, aerobic Facultative anaerobe |
| Yeast (*Candida*) | Dimorphic fungus |
| MCR-1 positive *E. coli* | GNR, aerobic Facultative anaerobe |
| *Burkholderia cepacia* group | Mixed GNR |
| HSV-1 | Virus |

For virtually all pathogens examined the anti-pathogenic compositions described herein have proven to be inhibit growth or kill the pathogen within a concentration range that does not negatively impact mammalian cells. These anti-pathogenic therapeutic compositions may generally include a mixture of one or more polar amino acids, one or more C11 fatty acids, and one or more anthraquinones, wherein the percentage of the one or more anthraquinone in the mixture is greater than 0.03% w/w of the mixture. Specifically, an anti-pathogenic therapeutic composition effective against gram negative and gram positive bacteria may include a mixture of one or more polar amino acids, one or more C11 fatty acids, and one or more anthraquinones, wherein the percentage of the one or more anthraquinone in the mixture is between 0.03% and 2.3% w/w of the mixture, the percentage of one or more polar amino acids is between 47% and 73% w/w of the mixture, and the percentage of one or more C11 fatty acid in the mixture is between 26% and 53% w/w of the mixture, further wherein the mixture is combined with an excipient, diluent, or carrier.

As mentioned, the one or more anthraquinones in the mixture may be any anthraquinone, including in particular one or more of: cassic acid, emodin (e.g., aloe emodin, aloeE), physcion, chrysophanol, dantron and/or cascarin. For example, the one or more anthraquinone in the mixture may include a mixture of: cassic acid and emodin; cassic acid and physcion; cassic acid and chysophaenol; cassic acid and dantron; cassic acid and cascarin; cassic acid and emodin and physcion; cassic acid and emodin and chrysophanol; cassic acid and emodin and dantron; cassic acid and emodin and cascarin; cassic acid and physcion and chrysophanol; cassic acid and physcion and dantron; cassic acid and physcion and cascarin; cassic acid and chrysophanol and dantron; cassic acid and chrysophanol and cascarin; cassic acid and dantron and cascarin; cassic acid and emodin and physcion and chrysophanol; cassic acid and emodin and physcion and dantron; cassic acid and emodin and physcion and cascarin; cassic acid and emodin and physcion and chrysophanol and dantron and cascarin; emodin and physcion; emodin and chrysophanol; emodin and dantron; emodin and cascarin; emodin and physcion and chrysophanol; emodin and physcion and dantron; emodin and physcion and cascarin; emodin and physcion and chrysophanol and dantron; emodin and physcion and chrysophanol and cascarin; emodin and physcion and chrysophanol and dantron and cascarin; physcion and chrysophanol; physcion and dantron; physcion and cascarin; physcion and chrysophanol and dantron; physcion and chrysophanol and cascarin; physcion and chrysophanol and dantron and cascarin; chrysophanol and dantron; chrysophanol and cascarin; chrysophanol and dantron and cascarin; and/or dantron and oxyclic acid. The total percentage of these one or more anthraquinones in the mixture may typically be between 0.03% and 2.3% w/w of the mixture. When multiple anthraquinones are included, the percentage of each anthraquinone may be equal or they may be different (e.g., 30% or more cassic acid, 40% or more cassic acid, 50% or more cassic acid, 60% or more cassic acid etc.). The percentage of one or more anthraquinone in the mixture may be between 0.1% and 1.0% w/w of the mixture.

As shown in FIG. 20 discussed above, in addition to cassic acid, other anthraquinones were tested for activity using an iodonitrotetrazolium chloride assay. Each anthraquinone was assayed for activity against one or more pathogen. In FIG. 20 activity was tested against MRSA growth. Inhibition of growth was shown with cassic acid, as well as emodin (aloe emodin), chrysophanol, dantron and oxcalic acid.

Antiviral Activity

Figure 23:
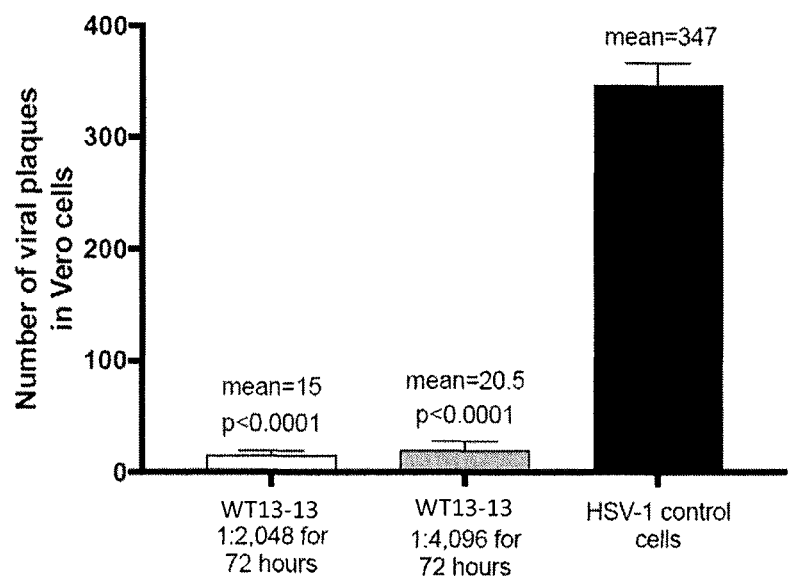
FIG. 23 illustrates the effect of an anti-pathogenic therapeutic composition as described herein on a virus (e.g., HSV-1 virus).

The anti-pathogenic therapeutic compositions described herein also exhibit antiviral activity. This is illustrated, for example, in FIG. 23, which illustrates the effect of the anti-pathogenic therapeutic composition (in this example a solution including a mixture of L-Arginine, undecylenic acid and cassic acid, wherein the percentage of cassic acid in the mixture is between 0.1% and 1.0% w/w of the mixture, the percentage of L-Arginine is between 47% and 73% w/w of the mixture, and the percentage of undecylenic acid in the mixture is between 26% and 53% w/w of the mixture. The compound also includes cetyl alcohol and water). As shown in FIG. 23, even highly diluted (e.g., 1:2048 and 1:4096) anti-pathogenic therapeutic compositions (having an initial concentration of cassic acid of approximately 2.0 mg/ml) were highly anti-viral, resulting in virtually no viral plaques with an extremely high level of significance. Based on assays such as those shown in the HSV-1 virus assay in FIG. 23, the inventors believe that the anti-pathogenic compounds described herein will have antiviral activity against a large number of viruses. In use, the anti-pathogenic agents described herein may be used to treat a patient (or a surface) to destroy viruses, by administering to said patient (or coating, dipping, spraying, etc. the surface), a therapeutically effective amount of any of the anti-pathogenic agents described herein. For example, the anti-pathogenic agent may include a mixture of L-Arginine, undecylenic acid and cassic acid, wherein the percentage of cassic acid in the mixture is between 0.03% and 2.3% w/w of the mixture, the percentage of L-Arginine is between 47% and 73% w/w of the mixture, and the percentage of undecylenic acid in the mixture is between 26% and about 53% w/w of the mixture, further wherein the mixture is combined with an excipient, diluent, or carrier.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An anti-pathogenic therapeutic composition comprising a mixture of L-Arginine, undecylenic acid and cassic acid, wherein the cassic acid is encapsulated in the undecylenic acid, and wherein the percentage of cassic acid in the mixture is greater than 0.03% w/w of the mixture.

2. The composition of claim 1, wherein the percentage of cassic acid in the mixture is between 0.03% and 2.3% w/w of the mixture.

3. The composition of claim 1, wherein the percentage of cassic acid in the mixture is between 0.1% and 1.0% w/w of the mixture.

4. The composition of claim 1, wherein the percentage of L-Arginine in the mixture is between 47% and 73% w/w of the mixture.

5. The composition of claim 1, wherein the percentage of undecylenic acid in the mixture is between 26% and 53% w/w of the mixture.

6. The composition of claim 1, wherein the percentage of L-Arginine in the mixture is about 62% w/w of the mixture, and the percentage of undecylenic acid is about 37.6% w/w of the mixture, and the percentage of cassic acid is about 0.4% w/w of the mixture.

7. The composition of claim 1, further comprising an excipient, diluent, or carrier.

8. The composition of claim 7, wherein said excipient, diluent, or carrier comprises cetyl alcohol and water.

9. The composition of claim 7, wherein said excipient, diluent, or carrier is configured for topical application.

10. The composition of claim 7, wherein said excipient, diluent, or carrier comprises an emulsifying agent.

11. The composition of claim 1, further comprising a cooling or heating additive.

12. The composition of claim 1, wherein the concentration of cassic acid in the composition is greater than 0.1 mg/ml.

13. The composition of claim 1, wherein the composition is configured as a liquid or emulsion in a form suitable for topical administration to a human.

14. The composition of claim 1, wherein the composition is configured for one or more of: oral, parenteral, intraperitoneal, transmucosal, transdermal, rectal, inhalable, and topical administration.

15. The composition of claim 1, wherein the composition is configured for coating a medical device.

16. An anti-pathogenic therapeutic composition effective against gram negative bacteria, the composition comprising a mixture of L-Arginine, undecylenic acid and cassic acid, wherein the cassic acid is encapsulated in the undecylenic acid, and wherein the percentage of cassic acid in the mixture is between 0.03% and 2.3% w/w of the mixture, the percentage of L-Arginine is between 47% and 73% w/w of the mixture, and the percentage of undecylenic acid in the mixture is between 26% and 53% w/w of the mixture.

17. An anti-pathogenic therapeutic composition effective against gram negative bacteria, the composition comprising a mixture of L-Arginine, undecylenic acid and cassic acid, wherein the cassic acid is encapsulated in the undecylenic acid, and wherein the percentage of cassic acid in the mixture is less than 5% w/w of the mixture, the percentage of L-Arginine is between 47% and 73% w/w of the mixture, and the percentage of undecylenic acid in the mixture is between 26% and 53% w/w of the mixture, further wherein the mixture is combined with an excipient, diluent, or carrier and the concentration of cassic acid in the composition is 0.1 mg/ml or greater.

* * * * *